United States Patent [19]
Asgharnejad et al.

[11] Patent Number: 6,123,964
[45] Date of Patent: Sep. 26, 2000

[54] WET GRANULATION FORMULATION OF A GROWTH HORMONE SECRETAGOGUE

[75] Inventors: Mandana Asgharnejad, Lansdale; Jerome Draper, Elkins Park; David Dubost, Collegeville; Michael Kaufman, New Hope; David Storey, Lansdale, all of Pa.

[73] Assignee: Merck & Co., Inc., Rahway, N.J.

[21] Appl. No.: 09/066,469

[22] PCT Filed: Oct. 23, 1996

[86] PCT No.: PCT/US96/17196

§ 371 Date: Oct. 27, 1998

§ 102(e) Date: Oct. 27, 1998

[87] PCT Pub. No.: WO97/15191

PCT Pub. Date: May 1, 1997

Related U.S. Application Data

[60] Provisional application No. 60/005,897, Oct. 27, 1995, and provisional application No. 60/005,901, Oct. 27, 1995.

[51] Int. Cl.$^7$ .......................................................... A61K 9/14
[52] U.S. Cl. .......................... 424/489; 424/468; 424/480; 424/464; 424/470
[58] Field of Search ........................... 424/489; 514/278; 546/18

[56] References Cited

U.S. PATENT DOCUMENTS 5,723,616  3/1998  Houghton et al. ...................... 546/18
5,767,124  6/1998  Draper et al. ........................... 514/278

Primary Examiner—Thurman K. Page
Assistant Examiner—William E. Benston, Jr.
Attorney, Agent, or Firm—J. Eric Thies; David L. Rose

[57] ABSTRACT

The present invention relates to a pharmaceutical composition and a process for the preparation of a tablet containing a growth hormone secretagogue as the active ingredient. The tablet is prepared by forming a powder blend of the active ingredient N-[1(R)-[(1,2-dihydro-1-methanesulfonyl-spiro[3H-indole-3,4'-piperdin]-1'-yl)carbonyl]-2-(phenylmethyloxy)ethyl]-2-amino-2-methyl-propanamide, or a pharmaceutically acceptable salt thereof, in particular the methanesulfonate salt, with a binder/diluent, a first diluent, a second diluent, a first portion of a disintegrant, and a lubricant; wet granulating the powder blend with a solution of ethanol/water to form granules; drying the granules to remove the ethanol/water; adding a second portion of a disintegrant; lubricating the granules; and compressing the dried granules into the desired tablet form. The present invention further relates to a novel amorphous form of the compound N-[1(R)-[(1,2-dihydro-1-methanesulfonyl-spiro[3H-indole-3,4'-piperdin]-1'-yl)carbonyl]-2-(phenylmethyloxy)ethyl]-2-amino-2-methylpropanamide methanesulfonate which is produced directly as a result of the process of tablet formulation.

28 Claims, No Drawings

WET GRANULATION FORMULATION OF A GROWTH HORMONE SECRETAGOGUE

CROSS REFERENCE TO RELATED APPLICATIONS

This application claims priority from PCT Application No. PCT/US96/17196, filed Oct. 23, 1996, which claims the benefit of U.S. Ser. No. 60/005,897, filed Oct. 27, 1995 and U.S. Ser. No. 60/005,901, filed Oct. 27, 1995.

FIELD OF THE INVENTION

The present invention relates to solid dosage formulations comprising a growth hormone secretagogue and process for their manufacture. More specifically, the invention relates to a wet granulation formulation of a growth hormone secretagogue compound. The present invention further relates to an amorphous form of a growth hormone secretagogue, processes for its preparation and uses thereof.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Various ways are known to release growth hormone. For example, chemicals such as arginine, L-3,4 dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. Non peptidal growth hormone secretagogues with a benzolactam structure are disclosed e.g., in U.S. Pat. Nos. 5,206,235, 5,283,241, 5,284,841, 5,310,737, 5,317,017, 5,374,721, 5,430,144, 5,434,261, 5,438,136 and PCT Publications WO 95/03289, WO 95/03290, WO 95/09633. Other growth hormone secretagogues are disclosed in PCT Patent Publications WO 94/11012, WO 94/13696, WO 94/19367, WO 95/13069 and WO 95/14666.

In particular, Examples 18, 19 and 55 of U.S. Pat. No. 5,536,716 (PCT Patent Publication WO 94/13696) and *Proc. Natl. Acad. Sci. USA*, 92, 7001–7005 (July 1995) disclose the compound N-[1(R)-[(1,2-dihydro-1-methanesulfonyl-spiro[3H-indole-3,4'-piperdin]-1'-yl)carbonyl]-2-(phenylmethyl-oxy)ethyl]-2-amino-2-methylpropanamide, and salts thereof, especially the methanesulfonate salt, which has the structure:

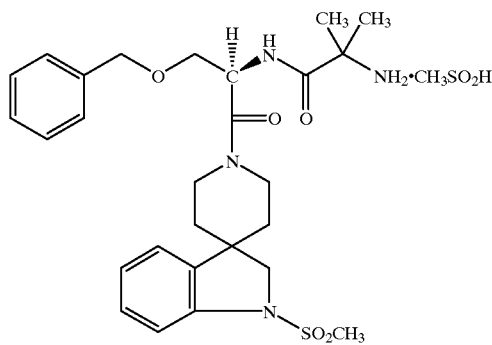

This compound is a growth hormone secretagogue which stimulates the release of growth hormone in humans and animals. This property can be utilized to promote the growth of food animals to render the production of edible meat products more efficient, and in humans, to treat physiological or medical conditions characterized by a deficiency in growth hormone secretion, and to treat medical conditions which are improved by the anabolic effects of growth hormone.

U.S. Pat. No. 5,536,716 and PCT Patent Publication WO 94/13696 disclose methods for preparing this compound (see Examples 18, 19 and 55). In particular, Example 55 states that the compound prepared by recrystallization from ethyl acetate-ethanol-water had a melting point of 166–168° C. *Proc. Natl. Acad. Sci. USA*, 92, 7001–7005 (July 1995) notes that this compound isolated as a monohydrate had a melting point of 168–170° C.

Standard methods for tablet formulation of the active ingredient such as direct compression suffer from problems. In particular, this compound is relatively unstable in standard pharmaceutical formulations. In addition, this compound as a bulk drug suffers from poor flow properties, nevertheless, wet granulation was discovered to overcome these difficulties preparing tablet formulations. Tablets prepared by the wet granulation method produced excellent content uniformity, coupled with suitable tablet dissolution and stability. The tablets of the present invention, prepared by wet granulation, possessed good hardness at normal machine pressures.

The present invention is also concerned with pharmaceutical formulations prepared by the subject process and their use in the treatment of certain disorders and diseases.

Exemplifying the present invention is the process comprising the steps of:

(1) forming a powder blend of the active ingredient with a binder/diluent, a first diluent, a second diluent, and a disintegrant, from 2 to 25 minutes using a mixer;

(2) wet granulating the powder blend by adding a solution of ethanol/water to the powder blend while mixing over a 1 to 30 minute period to form granules;

(3) drying the granules to remove the ethanol/water with heated air in a fluid bed dryer or tray dryer for 10 minutes to 24 hours;

(4) milling the dried granules to a uniform size;

(5) adding and blending a disintegrant with the dried milled particles for 2 to 30 minutes;

(6) adding and blending a lubricant to the mixture containing the disintegrant for 30 seconds to 20 minutes; and (7) compressing the lubricated granules mixture into a desired tablet form.

Further illustrating the invention is the process wherein the active ingredient is N-[1(R)-[(1,2-dihydro-1-methanesulfonylspiro[3H-indole-3,4'-piperdin]-1'-yl)carbonyl]-2-(phenylmethyloxy)ethyl)-2-amino-2-methylpropanamide methanesulfonate.

Additional illustrations of the invention include the process wherein: the binder/diluent is pregelatinized starch; the first diluent is microcrystalline cellulose; the second diluent is calcium phosphate dibasic; the disintegrant is croscarmellose sodium; and the lubricant is magnesium stearate. Preferably, the solution of ethanol/water is in the range of 0% to 80% ethanol in water (w/w), more preferably in the range of 5% to 75% ethanol/water (w/w) and even more preferably approximately 25% ethanol/75% water (w/w).

A further illustration of the invention is the foregoing process further comprising the step of applying a coating to the tablet. More particularly illustrating the invention is the process wherein coating the tablet is accomplished by:

(1) dry blending titanium dioxide (optionally mixed with talc) with hydroxypropyl methylcellulose and hydroxypropyl cellulose to form a dry powdered blend;

(2) adding the dry powdered blend to water to form a slurry;

(3) adding water to the slurry with stirring to form a suspension; and (4) applying the suspension to the tablets.

More specifically exemplifying the invention is the process comprising the steps of:

(1) forming a powder blend of the active ingredient with pregelatinized starch, microcrystalline cellulose, calcium phosphate dibasic, and croscarmellose sodium, in a mixer for about 3 to 25 minutes;

(2) wet granulating the powder blend by adding a solution of 25% ethanol/75% water (w/w) to the powder blend while mixing over a 1 to 30 minute period to form granules;

(3) drying the granules on a tray dryer or a fluid bed dryer for about 1 to 12 hours to remove the ethanol/water;

(4) milling the dried granules to a uniform size using a Quadro Comill or Fitz type mill;

(5) adding and blending croscarmellose sodium with the dried milled particles for about 5 to 30 minutes;

(6) adding and blending magnesium stearate to the mixture containing the croscarmellose sodium with a V blender for about 1 to 5 minutes; and (7) compressing the lubricated granules mixture into a desired tablet form.

Another example of the invention is the process wherein the active ingredient is N-[1(R)-[(1,2-dihydro-1-methanesulfonyl-spiro[3H-indole-3,4'-piperdin]-1'-yl)carbonyl]-2-(phenylmethyloxy)-ethyl]-2-amino-2-methylpropanamide methanesulfonate.

In a subclass is the foregoing process further comprising the step of coating the tablet. Further exemplifying the invention is the foregoing process further comprising the steps of:

(1) dry blending titanium dioxide (optionally mixed with talc) with hydroxypropyl methylcellulose and hydroxypropyl cellulose to form a dry powdered blend;

(2) adding the dry powdered blend to water to form a slurry;

(3) adding water to the slurry with stirring to form a suspension; and (4) applying the suspension to the tablets.

An additional illustration of the present invention is a solid dosage form containing an active ingredient of N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide, or a pharmaceutically acceptable salt thereof, in particular the methanesulfonate salt, wherein the dosage form is prepared by the process.

The present invention further relates to a novel amorphous form of the compound N-[1(R)-[(1,2-dihydro-1-methane-sulfonyl-spiro[3H-indole-3,4'-piperdin]-1'-yl)carbonyl]-2-(phenylmethyloxy)ethyl]-2-amino-2-methylpropanamide methanesulfonate. This amorphous form is produced directly as a result of the instant process of tablet formulation.

The amorphous form of N-[1(R)-[(1,2-dihydro-1-methanesulfonyl-spiro[3H-indole-3,4'-piperdin]-1'-yl)carbonyl]-2-(phenylmethyl-oxy)ethyl]-2-amino-2-methylpropanamide methanesulfonate exhibits a lack of crystallinity. The lack of crystallinity was confirmed by X-ray analysis wherein he X-ray diffraction pattern showed an amorphous halo.

The X-ray powder diffraction (XRPD) pattern was collected using a Phiulips APD3720 Automated Powder Diffraction instrument with copper Kα radiation. Measurements were made from 2° to 40° (2 theta) with the sample maintained at ambient room temperature.

In addition, examination of the amorphous form under microscopy showed no biorefringence.

The amorphous form may be prepared by evaporating a concentrated solution of N-[1(R)-[(1,2-dihydro-1-methanesulfonyl-spiro[3H-indole-3,4'-piperdin]-1'-yl)carbonyl]-2-(phenylmethyloxy)ethyl]-2-amino-2-methylpropanamide methanesulfonate in 25% aqueous ethanol (980 mg/ml) at 40° C. to give a solid.

Granulation is the process of adding a solvent, such as water or water/ethanol, to a powder mixture until granules are formed. The granulation step may be varied from 2 to 35 minutes, preferably 3 to 10 minutes, most preferably 4 to 8 minutes. Preferably, the granules are dried using a fluid bed dryer or tray dryer. Milling of the dried granules is accomplished using a Quadro Comill or Fitz mill. The lubrication step is the process of adding lubricant to the mixture. The lubrication step may be varied from 30 seconds to 20 minutes, preferably about 1 minute.

The disclosed process may be used to prepare solid dosage forms, particularly tablets or granules, for medicinal administration.

The term "tablet," as used herein, is intended to encompass compressed pharmaceutical dosage formulations of all shapes and sizes, whether coated or uncoated. Substances which may be used for coating include hydroxypropyl methylcellulose (HPMC), hydroxypropyl cellulose (HPC), titanium dioxide, talc, sweeteners and colorants.

The term "active ingredient," as used herein includes both the free base N-[1(R)-[(1,2-dihydro-1-methane-sulfonyl-spiro[3H-indole-3,4'-piperdin]-1'-yl)carbonyl)-2-(phenyl-methyl-oxy)ethyl]-2-amino-2-methyl-propanamide, as well as the pharmaceutically acceptable salts thereof, in particular, N-[1(R)-f(1,2-dihydro-1-methane-sulfonyl-spiro[3H-indole-3,4'-piperdin]-1'-yl)carbonyl]-2-(phenyl-methyl-oxy)ethyl]-2-amino-2-methyl-propanamide methanesulfonate and crystal forms thereof. A preferred crystal form for use in the present invention is that designated Form I.

Preferred diluents include: lactose, microcrystalline cellulose, calcium phosphate(s), mannitol, powdered cellulose, pregelatinized starch and other suitable diluents (see, e.g., Remington's Pharmaceutical Sciences, 18th Edition, 1990, p. 1635). Microcrystalline cellulose and calcium phosphate dibasic, are particularly preferred. Specifically, microcrystalline cellulose NF, especially Avicel PH101, the trademarked name for microcrystalline cellulose NF manufactured by FMC Corp. is preferred.

Preferred binders include pregelatinized starch, hydroxypropyl methylcellulose, hydroxypropyl cellulose, polyvinylpyrrolidone (PVP) and other known binders (see, e.g., Remington's Pharmaceutical Sciences, 18th Edition, 1990, pp. 1635–1636) and mixtures thereof. Most preferably, pregelatinized starch as employed as a binder. Specifically, starch pregelatinized NF 1500 manufactured by Colorcon Corporation is most preferred.

The disintegrant may be one or more of several starches, clays, celluloses, algins, gums or crosslinked polymers known to those skilled in the art (See, e.g., Remington's Pharmaceutical Sciences, 18th Edition, 1990, p. 1637) and mixtures thereof. Preferably, one or more of several modified starches or modified cellulose polymers, such as microcrystalline cellulose and croscarmellose sodium, are used. Croscarmellose sodium Type A, commercially available under the trade name "Ac-di-sol," is particularly preferred.

Preferred lubricants include magnesium stearate, zinc stearate, calcium stearate, stearic acid, surface active agents such as sodium lauryl sulfate, magnesium lauryl sulfate, propylene glycol, sodium dodecane sulfonate, sodium oleate sulfonate and sodium laurate mixed with stearates and talc, sodium stearyl fumarate, hydrogenated vegetable oils, glyceryl palmitostearate, glyceryl behenate, sodium benzoate, mineral oil, talc and other known lubricants (see, e.g., Remington's Pharmaceutical Sciences, 18th Edition, 1990, pp. 1636–1637), and mixtures thereof. An especially preferred lubricant is magnesium stearate.

The active ingredient, N-[1(R)-[(1,2-di-hydro-1-methanesulfonylspiro[3H-indole-3,4'-piperdin]-1'-yl)carbonyl)-2-(phenylmethyloxy)ethyl]-2-amino-2-methylpropanamide, may be prepared according to the methods disclosed in U.S. Pat. No. 5,536,716, PCT Patent Publication WO 94/13696 and the methods disclosed herein.

The pharmaceutically acceptable salts of N-[1(R)-[(1,2-dihydro-1-methane-sulfonyl-spiro[3H-indole-3,4'-piperdin]-1'-yl)carbonyl]-2-(phenyl-methyl-oxy)ethyl]-2-amino-2-methylpropanamide may be employed in the instant invention. Examples of pharmaceutically acceptable salts include the pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like.

The pharmaceutical compositions of the present invention comprise 0.1 to 50% by weight of an active ingredient, N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide, or a pharmaceutically acceptable salt thereof, preferably N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide methanesulfonate; 0 to 77% by weight of a binder/diluent; 0 to 77% by weight of a first diluent; 0 to 77% by weight of a second diluent; 0 to 6% by weight of a disintegrant; and 0 to 5% by weight of a lubricant. It will be appreciated by one skilled in the art that the sum of the proportions of the active ingredient, the binder/diluent, the first diluent, the second diluent, the disintegrant, and the lubricant are not greater than 100% by weight.

More specifically, the binder/diluent is selected from hydroxy-propyl methylcellulose, hydroxypropyl cellulose, pregelatinized starch or polyvinylpyrrolidone; the first and second diluents are independently selected from lactose, microcrystalline cellulose, calcium phosphate dibasic, mannitol, powdered cellulose or pregelatinized starch; the disintegrant is selected from microcrystalline or croscarmellose sodium; and the lubricant is selected from magnesium stearate, calcium stearate, steric acid or a surface active agent.

In a specific embodiment, the binder/diluent is pregelatinized starch; the first diluent is microcrystalline cellulose; the second diluent is calcium phosphate dibasic; the disintegrant is croscarmellose sodium; and the lubricant is magnesium stearate.

The pharmaceutical compositions of the present invention are preferably in the form of tablets. The tablets may be, for example, from 50 mg to 1.0 g in net weight, preferably 100 to 800 mg net weight, more preferably 100 to 400 mg net weight.

Preferred pharmaceutical compositions comprise about 1 to 30% by weight of the active ingredient; about 20 to 40% by weight of pregelatinized starch; about 10 to 20% by weight of microcrystalline cellulose; about 20 to 50% by weight of calcium phosphate dibasic; about 5 to 15% by weight of croscarmellose sodium; and about 0.05 to 5% by weight of magnesium stearate.

It will be appreciated by one skilled in the art that the sum of the above proportions of the active ingredient, pregelatinized starch, microcrystalline cellulose, calcium phosphate dibasic, croscarmellose sodium, and magnesium stearate are not greater than 100% by weight.

More preferred pharmaceutical compositions in accordance with the present invention include those comprising the noted ingredients:

(1) about 1 to 2% by weight of the active ingredient; about 25 to 35% by weight of pregelatinized starch; about 10 to 20% by weight of microcrystalline cellulose; about 45–55% by weight of calcium phosphate dibasic; about 4 to 8% by weight of croscarmellose sodium; and about 0.1 to 1% by weight of magnesium stearate.

(2) about 5 to 10% by weight of the active ingredient, about 25 to 35% by weight of pregelatinized starch; about 10 to 20% by weight of microcrystalline cellulose; about 40 to 50% by weight of calcium phosphate dibasic; about 4 to 8% by weight of croscarmellose sodium; and about 0.1 to 1% by weight of magnesium stearate.

(3) about 25 to 35% by weight of the active ingredient, about 15 to 25% by weight of pregelatinized starch; about 10 to 20% by weight of microcrystalline cellulose; about 15–25% by weight of calcium phosphate dibasic; about 10 to 20% by weight of croscarmellose sodium; and about 0.1 to 1% by weight of magnesium stearate.

It will be appreciated by one skilled in the art that the sum of the above proportions of the active ingredient, pregelatinized starch, microcrystalline cellulose, calcium phosphate dibasic, croscarmellose sodium, and magnesium stearate are not greater than 100% by weight.

Especially referred pharmaceutical compositions as envisioned for commercial development are as follows:

Tablets of 1.0 mg potency free base:

about 1.18% by weight of active ingredient as the methanesulfonate salt; about 30.0% by weight of pregelatinized starch; about 15.0% by weight of microcrystalline cellulose; about 47.3% by weight of calcium phosphate dibasic; about 6.0% by weight of croscarmellose sodium; and about 0.5% by weight of magnesium stearate. This composition comprises about 1.2 mg of active ingredient as the methanesulfonate salt; about 30 mg of pregelatinized starch; about 15 mg of microcrystalline cellulose; about 47.3 mg of calcium phosphate dibasic; about 6.0 mg of croscarmellose sodium; and about 0.5 mg of magnesium stearate per dosage unit.

Optionally, the 1.0 mg potency tablet may be coated with a coating comprising about 0.8% by weight of hydroxypropyl methylcellulose; about 0.8% by weight of hydroxypropyl cellulose; about 0.32% by weight of titanium dioxide; and about 0.08% by weight of talc (as a percentage of the core tablet weight).

Tablets of 5.0 mg potency free base:

about 1.48% by weight of active ingredient as the methanesulfonate salt; about 30.0% by weight of pregelatinized starch; about 15.0% by weight of microcrystalline cellulose; about 47.0% by weight of calcium phosphate dibasic; about 6.0% by weight of croscarmellose sodium; and about 0.5% by weight of magnesium stearate. This composition comprises about 6 mg of active ingredient as the methanesulfonate salt; about 120 mg of pregelatinized starch; about 60 mg of microcrystalline cellulose; about 188 mg of calcium phosphate dibasic; about 24 mg of croscarmellose sodium; and about 2 mg of magnesium stearate per dosage unit.

Optionally, the 5.0 mg potency tablet may be coated with a coating comprising about 0.8% by weight of hydroxypropyl methylcellulose; about 0.8% by weight of hydroxypropyl cellulose; about 0.32% by weight of titanium dioxide; and about 0.08% by weight of talc (as a percentage of the core tablet weight).

Tablets of 25 mg potency free base:

about 7.39% by weight of active ingredient as the methanesulfonate salt; about 282% by weight of pregelatinized starch; about 14.2% by weight of microcrystalline cellulose; about 43.6% by weight of calcium phosphate dibasic; about 6.0% by weight of croscarmellose sodium; and about 0.5% by weight of magnesium stearate. This composition comprises about 30 mg of active ingredient as the methanesulfonate salt; about 113 mg of pregelatinized starch; about 57 mg of microcrystalline cellulose; about 174 mg of calcium phosphate dibasic; about 24 mg of croscarmellose sodium; and about 2 mg of magnesium stearate per dosage unit.

Optionally, the 25 mg potency tablet may be coated with a coating comprising about 0.8% by weight of hydroxypropyl methylcellulose; about 0.8% by weight of hydroxypropyl cellulose; about 0.32% by weight of titanium dioxide; and about 0.08% by weight of talc (as a percentage of the core tablet weight).

Tablets of 100 mg potency free base:

about 29.5% by weight of active ingredient as the methanesulfonate salt; about 19.5% by weight of pregelatinized starch; about 15.0% by weight of microcrystalline cellulose; about 20.4% by weight of calcium phosphate dibasic; about 15.0% by weight of croscarmellose sodium; and about 0.5%o by weight of magnesium stearate. This composition comprises about 118 mg of active ingredient as the methanesulfonate salt; about 78 mg of pregelatinized starch; about 60 mg of microcrystalline cellulose; about 82 mg of calcium phosphate dibasic; about 60 mg of croscarmellose sodium; and about 2 mg of magnesium stearate per dosage unit.

Optionally, the 100 mg potency tablet may be coated with a coating comprising about 0.8% by weight of hydroxypropyl methylcellulose; about 0.8% by weight of hydroxypropyl cellulose; about 0.32% by weight of titanium dioxide; and about 0.08% by weight of talc (as a percentage of the core tablet weight).

The tablets of the 1.0 mg potency are preferably formulated in an 100 mg tablet by using 30 μl of a solution of 25% ethanol/75% water per tablet. The tablets of the 5.0 mg potency are preferably formulated in an 400 mg tablet by using 120 μl of a solution of 25% ethanol/75% water per tablet. The tablets of the 25 mg potency are preferably formulated in an 400 mg tablet by using 120 μl of a solution of 25% ethanol/75% water per tablet. The tablets of the 100 mg potency are preferably formulated in an 400 mg tablet by using 120 μl of a solution of 25% ethanol/75% water per tablet.

In a particularly preferred embodiment, the tablet formulations of the instant invention are coated. In the pharmaceutical compositions envisioned for commercial development described above, the tablets of 1.0 mg, 5.0 mg, 25 mg and 100 mg potency free base are coated with about 0.8% by weight of hydroxypropyl methylcellulose; about 0.8% by weight of hydroxypropyl cellulose; about 0.32% by weight titanium dioxide; and about 0.08% by weight of purified talc.

In the most preferred embodiment, the active ingredient in the above-described pharmaceutical compositions is N-[1(R)-[(1,2-dihydro-1-methanesulfonylspiro[3H-indole-3,4'-piperdin]-1'-yl)carbonyl]-2-(phenylmethyloxy)ethyl)-2-amino-2-methylpropanamide methanesulfonate.

The compositions of the present invention are in a form for oral administration and may take the form of tablets, capsules, granules, powders, tablets or granules for buccal administration, or liquid preparations such as suspensions. Granules and powders may be ingested directly, or dispersed in water or other suitable vehicle prior to administration. Capsules may be of the hard or soft gelatin type, including soft gelatin capsules.

The pharmaceutical compositions of the present invention may also contain other excepients conventional in the art such as flavorings, sweeteners, and the like. Suitable flavorings include for example fruit flavors or natural or synthetic mint or peppermint flavors. Suitable sweeteners include for example sugar, saccharin or aspartame.

The utility of the active ingredient of the formulation of the present invention as growth hormone secretagogues may be demonstrated by methodology known in the art, such as an assay described by Smith, et al., *Science*, 260, 1640–1643 (1993) (see text of FIG. 2 therein). In particular, the active ingredient used in the formulation the present invention had activity as a growth hormone secretagogue in the aforementioned assay. Such a result is indicative of the activity of the formulation of the present invention as a growth hormone secretagogue.

The formulations of the present invention may be administered to animals, including man, to release growth hormone in vivo. For example, the formulations can be administered to commercially important animals such as swine, cattle, sheep and the like to accelerate and increase their rate and extent of growth, to improve feed efficiency and to increase milk production in such animals. In addition, these formulations can be administered to humans in vivo as a diagnostic tool to directly determine whether the pituitary is capable of releasing growth hormone. For example, the formulation of the present invention can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, the compound N-[1(R)-[(1,2-dihydro-1-methane-sulfonyl-spiro[3H-indole- 3,4'-piperdin]-1'-yl)carbonyl]-2-(phenyl-methyl-oxy)ethyl]-2-amino-2-methyl-propanamide in association with a pharmaceutical carrier or diluent. Optionally, the active ingredient of the pharmaceutical compositions may comprise an anabolic agent in addition to the compound N-[1(R)-[(1,2-dihydro-1-methane-sulfonyl-spiro[3H-indole-3,4'-piperdin]-1'-yl)carbonyl]-2-(phenyl-methyl-oxy)ethyl]-2-amino-2-methyl-propanamide or another composition which exhibits a different activity, e.g., an antibiotic growth permittant or an agent to treat osteoporosis or in combination with a corticosteroid to minimize the catabolic side effects or with other pharmaceutically active materials wherein the combination enhances efficacy and minimizes side effects.

Growth promoting and anabolic agents include, but are not limited to TRH, diethylstilbesterol, amino acids, estrogens, β-agonists, theophylline, anabolic steroids, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the formulations of this invention is in combination with other growth hormone secretagogues such as the growth hormone releasing peptides GHRP-6, GHRP-1 as described in U.S. Pat. No. 4,411,890 and publications WO 89/07110, WO 89/07111 and B-HT920 as well as hexarelin and GHRP-2 as described in WO 93/04081 or growth hormone releasing hormone (GHRH, also designated GRF) and its analogs or growth hormone and its analogs or somatomedins including IGF-1 and IGF-2 or α-adrenergic agonists such as clonidine or serotonin 5HTID agonists such as sumitriptan or agents which inhibit somatostatin or its release such as physostigmine and pyridostigmine. In particular, the formulations of this invention may be used in combination with growth hormone releasing factor, an analog of growth hormone releasing factor, IGF-1, or IGF-2. For example, a formulation of the present invention may be used in combination with IGF-1 for the treatment or prevention of obesity. In addition, a formulation of this invention may be employed in conjunction with retinoic acid to improve the condition of musculature and skin that results from intrinsic aging.

As is well known to those skilled in the art, the known and potential uses of growth hormone are varied and multitudinous. The administration of the formulations of this invention for purposes of stimulating the release of endogenous growth hormone can have the same effects or uses as growth hormone itself. These varied uses of the present formulations thus may be summarized as follows: stimulating growth hormone release in elderly humans; treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treatment of obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia, treatment of peripheral neuropathies; replacement of growth hormone in stressed patients; treatment of osteochondrody-splasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; to stimulate thymic development and prevent the age-related decline of thymic function; adjunctive therapy for patients on chronic hemodialysis; treatment of immunosuppressed patients and to enhance antibody response following vaccination; increasing the total lymphocyte count of a human, in particular, increasing the $T_4/T_8$-cell ratio in a human with a depressed $T_4/T_8$-cell ratio resulting, for example, from physical trauma, such as closed head injury, or from infection, such as bacterial or viral infection, especially infection with the human immunodeficiency virus; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock; and stimulation of wool growth in sheep. Further, the instant compounds are useful for increasing feed efficiency, promoting growth, increasing milk production and improving the carcass quality of livestock. Likewise, the instant formulations are useful in a method of treatment of diseases or conditions which are benefited by the anabolic effects of enhanced growth hormone levels.

In particular, the instant formulations are useful in the prevention or treatment of a condition selected from the group consisting of: osteoporosis; catabolic illness; immune deficiency, including that in individuals with a depressed $T_4/T_8$ cell ratio; hip fracture; musculoskeletal impairment in the elderly; growth hormone deficiency in adults or in children; obesity; cachexia and protein loss due to chronic illness such as AIDS or cancer; and treating patients recovering from major surgery, wounds or burns, in a patient in need thereof.

In addition, the instant formulations may be useful in the treatment of illnesses induced or facilitated by corticotropin releasing factor or stress- and anxiety-related disorders, including stress-induced depression and headache, abdominal bowel syndrome, immune suppression, HIV infections, Alzheimer's disease, gastrointestinal disease, anorexia nervosa, hemorrhagic stress, drug and alcohol withdrawal symptoms, drug addiction, and fertility problems.

It will be known to those skilled in the art that there are numerous compounds now being used in an effort to treat the diseases or therapeutic indications enumerated above. Combinations of these therapeutic agents some of which have also been mentioned above in and with the formulations of this invention will bring additional, complementary, and often synergistic properties to enhance the growth promotant, anabolic and desirable properties of these various therapeutic agents. In these combinations, the therapeutic agents and the active ingredient in the formulations of this invention may be independently present in dose ranges from one one-hundredth to one times the dose levels which are effective when these compounds and active ingredients are used singly.

Combined therapy to inhibit bone resorption, prevent osteoporosis and enhance the healing of bone fractures can be illustrated by combinations of bisphosphonates and the formulations of this invention. The use of bisphosphonates for these utilities has been reviewed, for example, by Hamdy, N. A. T., Role of Bisphosphonates in Metabolic Bone Diseases, *Trends in Endocrinol. Metab.*, 4, 19–25 (1993). Bisphosphonates with these utilities include alendronate, tiludronate, dimethyl-APD, risedronate, etidronate, YM-175, clodronate, pamidronate, and BM-210995. According to their potency, oral daily dosage levels of the bisphosphonate of between 0.1 mg and 5 g and daily dosage levels of the active ingredient of the formulation of this invention of between 0.01 mg/kg to 20 mg/kg of body weight are administered to patients to obtain effective treatment of osteoporosis.

In the case of alendronate daily oral dosage levels of 0.1 mg to 50 mg are combined for effective osteoporosis therapy with 0.01 mg/kg to 20 mg/kg of the active ingredient employed in the formulation of this invention. Osteoporosis and other bone disorders may also be treated with the formulations of this invention in combination with calcitonin, estrogens, raloxifene and calcium supplements such as calcium citrate.

Anabolic effects especially in the treatment of geriatric male patients are obtained with formulations of this invention in combination with anabolic steroids such as oxymetholone, methyltesterone, fluoxymesterone and stanozolol.

The pharmaceutical tablet compositions of the present invention may also contain one or more additional formulation ingredients selected from a wide variety of excipients (also referred to as "additives") known in the pharmaceutical formulation art. According to the desired properties of the tablet, any number of additives may be selected, alone or in combination, based upon their known uses in preparing tablet compositions. Such additives include, but are not limited to, diluents, binders, compression aids, disintegrants, lubricants, flavors, flavor enhancers, sweeteners and preservatives. Due to the bitter taste of the active ingredient, the inclusion of a sweetener may be desired.

The dosage of active ingredient in the compositions of this invention may be varied; however, it is necessary that the amount of the active ingredient be such that a suitable dosage form is obtained. The selected dosage depends upon the desired therapeutic effect, on the route -of administration, and on the duration of the treatment. Generally, dosage levels of between 0.0001 to 10 mg/kg. of body weight daily are administered to patients and animals, e.g., mammals, to obtain effective release of growth hormone. Preferably, the dosage level will be about 0.001 to about 25 mg/kg per day; more preferably about 0.01 to about 10 mg/kg per day.

Methods for preparing the formulations of the present invention, as well as the active ingredient are illustrated in the following Examples. The following examples are given for the purpose of illustrating the present invention and shall not be construed as being limitations on the scope or spirit of the instant invention.

EXAMPLE 1

N-[1(R)-[(1,2-Dihydro-1-methanesulfonylspiro[3H-indole-3,4'-piperdin]-1'-yl)carbonyl]-2-(phenylmethyloxy)ethyl]-2-amino-2-methylpropanamide Step A: 1,2-Dihydro-1-methanesulfonylspiro[3H-indole-3,4'-piperdine]hydrochloride To a solution of 1.20 g (5.8 mmol) of 1'-methyl-1,2-dihydro-spiro[3H-indole-3,4'-piperdine] (prepared as described by H. Ong, et al., *J. Med. Chem.*, 23, 981–986 (1983)) in 20 mL of dry dichloromethane at 0° C. was added triethylamine (0.90 mL; 6.4 mmol) and methanesulfonyl chloride (0.49 mL; 6.35 mmol) and stirred for 30 min. The reaction mixture was poured into 15 mL of saturated aqueous sodium bicarbonate solution and extracted with dichloromethane (2×10 mL). The combined organics were washed with brine (20 mL), dried over anhydrous potassium carbonate, filtered and the solvent removed under reduced pressure to yield 1.44 g of the methanesulfonamide derivative as pale yellow oil which was used without purification.

To a solution of above crude product in 20 mL of dry 1,2-dichloroethane at 0° C. was added 1.0 mL (9.30 mmol) of 1-chloroethyl chloroformate, and then stirred at RT for 30 min and finally at reflux for 1 h. The reaction mixture was concentrated to approximately one third of the volume and then diluted with 20 mL of dry methanol and refluxed for 1.5 h. The reaction was cooled to RT and concentrated to approximately one half of the volume. The precipitate was filtered and washed with a small volume of cold methanol. This yielded 1.0 g of the piperidine HCl salt as a white solid. The filtrate was concentrated and a small volume of methanol was added followed by ether. The precipitated material was once again filtered, washed with cold methanol, and dried. This gave an additional 0.49 g of the desired product. Total yield 1.49 g (70%).

$^1$H NMR (CDCl$_3$, 200 MHz) δ 7.43–7.20 (m, 3H), 7.10 (dd, 1H), 3.98 (bs, 2H), 3.55–3.40 (bd, 2H), 3.35–3.10 (m, 2H), 2.99 (s, 3H), 2.15 (t, 2H), 2.00 (t, 2H).

Step B: N-[1(R)-[(1,2-Dihydro-1-methanesulfonylspiro[3H-indole-3,4'-piperdin]-1'-yl)carbonyl]-2-(phenylmethyloxy)ethyl]-2-[(1,1-dimethylethoxy)carbonyl]amino-2-methylpropanamide To 0.35 g (1.15 mmol) of (2R)-2-[(1,1-dimethylethoxy)carbonyl]amino-3-[2-(phenylmethyloxy)ethyl]-1-propanoic acid in 13 mL of dichloromethane was added 1,2-dihydro-1-methanesulfonylspiro-[3H-indole-3,4'-piperdine) hydrochloride (0.325 g; 1.07 mmol), 0.18 -mL (1.63 mmol) of N-methylmorpholine, 0.159 g (1.18 mmol) of 1-hydroxybenztriazole(HOBT) and stirred for 15 min. EDC (0.31 g; 1.62 mol) was added and stirring was continued for 1 h. An additional 60 μL of N-methylmorpholine was added and stirred for 45 min. The reaction mixture was poured into 5 mL of water and the organic layer was separated. The organic layer was washed with 5 mL of 0.5N aqueous hydrochloric acid and 5 mL of saturated aqueous sodium bicarbonate solution. The combined organics were dried over anhydrous magnesium sulfate, and concentrated to yield 0.627 g of the product as a yellow foam which was used without purification.

To a 0.627 g (1.07 mmol) of the above product in 5 mL of dichloromethane was added 1.0 mL of trifluoroacetic acid and stirred at RT for 75 min. An additional 1.00 mL of trifluoroacetic acid was added and stirred for 10 min. The reaction mixture was concentrated, diluted with 5.0 mL of dichloromethane and carefully basified by pouring into 10 mL of 10% aqueous sodium carbonate solution. The organic layer was separated and the aqueous layer was further extracted with 2×15 mL of dichloromethane. The combined organics were washed with 5 mL of water, dried over potassium carbonate, filtered and concentrated to give the 0.486 g of the amine as a light yellow foam which was used without purification.

To 0.486 g (1.01 mmol) of the amine and 10 mL of dichloromethane was added 0.26 g (1.28 mmol) of 2-[(1,1-dimethylethoxy)carbonyl]amino-2-methyl-propanoic acid, 0.173 g (1.28 mmol) of 1-hydroxybenztriazole (HOBT) and EDC (0.245 g; 1.28 mol) and stirred at RT overnight. The reaction mixture was poured into 5.0 mL of water and the organic layer was separated. The aqueous layer was back extracted with 5 mL of dichloromethane. The combined organics were washed with 5.0 mL of 0.5N aqueous hydrochloric acid, 5 mL of saturated aqueous sodium bicarbonate solution and dried over anhydrous magnesium sulfate, and concentrated to yield 0.751 g of the crude product as a yellow foam. A solution of this crude product in dichloromethane was chromatographed on 25 g of silica gel and eluted first with hexanes/acetone/dichloromethane (70/25/5) and then with hexanes/acetone/dichloromethane (65/30/5). This gave 0.63 g of the title compound as a white solid.

$^1$H NMR (CDCl$_3$, 400 MHz) Compound exists as a 3:2 mixture of rotamers δ 7.40–7.10 (m, 6H), 7.06 (d, 1/3H), 7.02 (t, 1/3H), 6.90 (t, 1/3H), 6.55 (d, 1/3H), 5.15 (m, 1H), 4.95 (bs, 1H), 4.63 (bd, 1/3H), 4.574.40 (m, 2 2/3 H), 4.10 (bd, 1/3H), 4.00 (bd, 1/3H), 3.82 (t, 1H), 3.78–3.62 (m, 2H), 3.60–3.50 (m, 1H), 3.04 (q, 1H), 2.87 (s, 1H), 2.86 (s, 2H), 2.80–2.60 (m, 1H), 1.90 (bs, 1H), 2.85–2.75 (m, 1H), 1.82–1.60 (m, 3H), 1.55–1.45 (m, 1H), 1.45 (s, 4H), 1.42 (s, 2H), 1.39 (s, 9H).

Step C: N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide hydrochloride To 0.637 g (0.101 mmol) of the intermediate from Step B in 5 mL of dichloromethane was added 2.5 mL of trifluoroacetic acid and stirred at RT for 30 min. The reaction mixture was concentrated to an oil, taken up in 10 mL of ethyl acetate and washed with 8 mL of 10% aqueous sodium carbonate solution. The aqueous layer was further extracted with 5 mL of ethyl acetate. The combined organics were washed with 10 mL of water, dried over magnesium sulfate, filtered and concentrated to give the 0.512 g of the free base as a white foam.

To 0.512 g of the free base in 5 mL of ethyl acetate at 0° C. was added 0.2 mL of saturated hydrochloric acid in ethyl acetate and stirred for 1.5 h. The white precipitate was filtered under nitrogen, washed with ether, and dried to give 0.50 g of the title compound as a white solid.

$^1$H NMR (400 MHz, CD$_3$OD) Compound exists as 3:2 mixture of rotamers. δ 7.40–7.28 (m, 4H), 7.25–7.17 (m, 2H), 7.08 (t, 1/3H), 7.00 (t, 1/3H), 6.80 (d, 1/3H), 5.16 (ddd, 1H), 4.60–4.42 (m, 3H), 4.05 (t, 1H), 3.90 (bs, 2H), 3.83–3.70 (m, 2H), 3.30–3.15 (m, 1H), 2.97 (s, 1H), 2.95 (s, 2H), 2.90–2.78 (m, 1H), 1.96 (t, 1/3H), 1.85–1.65 (m, 4H), 1.63 (s, 2H), 1.60 (s, 4H).

EXAMPLE 2

N-[1(R)-[(1,2-Dihydro-1-methanesulfonylspiro[3H-indole-3,4'-piperdin]-1'-yl) carbonyl]-2-(phenylmethyloxy)ethyl]-2-amino-2-methylpropanamide Step A: (2R)-[[[-2-(1,1-dimethylethoxy)carbonyl]amino]-2,2-dimethyl-1-oxoethyl]amino-2-(phenylmethoxy)ethyl]-1-propanoic acid allyl ester Prepared from (2R)-2-[(1,1-dimethylethoxy)carbonyl]-amino-3-(phenylmethyloxy)ethyl-propanoic acid and allyl alcohol by carrying out the coupling reaction in CH$_2$Cl$_2$ in the presence of EDC and DMAP.

$^1$H NMR (400 MHz, CDCl$_3$) δ 7.25 (s, 5H), 5.8 (m, 1H), 5.2 (dd, 2H), 5.0 (bs, 1H), 4.7 (m, 1H), 4.6 (m, 2H), 4.4 (dd, 2H), 3.9 (dd, 1H), 3.6 (dd, 1H), 1.45 (d, 6H), 1.39 (s, 9H).

Step B: (2R)-[[[-2-(1,1-dimethylethoxy)carbonyl]amino]-2,2-dimethyl-1-oxoethyl] amino-2-(phenylmethyloxy)ethyl)-1-propanoic acid To a stirred solution of the crude intermediate obtained in Step A (6.7 g, 15.9 mmol), tetrakis (triphenylphosphine)-palladium (1.8 g, 0.1 eq) and, triphenyl phosphine (1.25 g, 0.3 eq) was added a solution of potassium-2-ethyl hexanoate (35 mL, 0.5M solution in EtOAc). The reaction mixture was stirred at room temperature under nitrogen atmosphere for 1 h and then diluted with ether (100 mL) and poured into ice-water. The organic layer was seperated and the aqueous fraction was acidified with citric acid (20%), then extracted with EtOAc. The EtOAc extracts were washed with brine, dried over magnesium sulfate, filtered and evaporated to give the title compound as a solid.

$^1$H NMR (400Hz, CD$_3$OD) δ 7.3 (s, 5H), 4.7 (m, 1H), 4.5 (s, 2H), 4.0 (m, 1H), 3.6 (m, 1H), 1.4 (d, 6H), 1.3 (s, 9H).

Step C: N-[(R)-[(1,2-Dihydro-1-methanesulfonylspiro[3H-indole-3,4'-piperdin]-1'-yl)carbonyl]-2-(phenylmethyloxy)ethyl]-2-[(1,1-dimethyl-ethoxy)carbonyl]amino-2-methyl-propanamide To a solution of 1.0 g (3.44 mmol) of 1-methanesulfonylspiro[indoline-3,4'-piperidine] hydrochloride, 1.44 g (3.78 mmol) of (2R)-[[-2-(1,1-dimethylethoxy)carbonyl)amino]-2,2-dimethyl-1-oxoethyl]-amino-2-(phenylmethyloxy)ethyl)-1-propanoic acid, N-methyl morpholine (0.58 mL; 5.20 mmol), and 1-hydroxybenztriazole (HOBT) (0.58 g; 3.78 mmol), in 50 mL of dichloromethane was added EDC (1.03 g; 5.20 mmol) and stirred at RT for 16 h. The reaction mixture was diluted with an additional 50 mL of dichloromethane and washed with aqueous sodium bicarbonate solution (50 mL), dried over anhydrous magnesium sulfate, filtered, and concentrated. Flash chromatography (50 g silica gel) of the crude oily residue gave 2.148 g (90%) of the desired material as a colorless foam.

$^1$H NMR (CDCl$_3$, 400 MHz) Compound exists as a 3:2 mixture of rotamers δ 7.40–7.10 (m, 6H), 7.06 (d, 1/3H), 7.02 (t, 1/3H), 6.90 (t, 1/3H), 6.55 (d, 1/3H), 5.15 (m, 1H), 4.95 (bs, 1H), 4.63 (bd, 1/3H), 4.574.40 (m, 2 2/3 H), 4.10 (bd, 1/3H), 4.00 (bd, 1/3H), 3.82 (t, 1H), 3.78–3.62 (m, 2H), 3.60–3.50 (m, 1H), 3.04 (q, 1H), 2.87 (s, 1H), 2.86 (s, 2H), 2.80–2.60 (m, 1H), 1.90 (bs, 1H), 2.85–2.75 (m, 1H), 1.82–1.60 (m, 3H), 1.55–1.45 (m, 1H), 1.45 (s, 4H), 1.42 (s, 2H), 1.39 (s, 9H).

Step D: N-[1(R)-[(1,2-Dihydro-1-methanesulfonylspiro[3H-indole-3,4'-piperdin]-1'-yl)carbonyl]-2-(phenylmethyloxy)ethyl]-2-amino-2-methylpropanamide hydrochloride To a solution of 2.148 g (3.41 mmol) of the intermediate from Step C in 10 mL of dichloromethane was added 5 mL of trifluoroacetic acid and stirred for 1 h. The reaction mixture was concentrated and basified with 100 mL of 5% aqueous sodium carbonate solution and extracted with dichloromethane (3×50 mL). The combined organics were washed with brine (50 mL), dried over anhydrous potassium carbonate, filtered, and concentrated to yield a colorless foam. To a solution of the foam in 25 mL of ethyl acetate at 0° C. was added 4 mL of 1 M solution of hydrochloric acid in ethyl acetate. The precipitate was filtered and washed first with ethyl acetate and then with ethyl acetate-ether (1:1), dried to yield 1.79 g (93%) of the title compound as a colorless solid.

$^1$H NMR (400 MHz, CD$_3$OD) Compound exists as 3:2 mixture of rotamers. δ 7.40–7.28 (m, 4H), 7.25–7.17 (m, 2H), 7.08 (t, 1/3H), 7) (t, 1/3H), 6.80 (d, 1/3H), 5.16 (ddd, 1H), 4.60–4.42 (m, 3H), 4.05 (1H), 3.90 (bs, 2H), 3.83–3.70 (m, 2H), 3.30–3.15 (m, 1H0, 2.97 (s, 1H), 2.95 (s, 2H), 2.90–2.78 (m, 1H), 1.96 (t, 1/3H), 1.85–1.65 (m, 4H), 1.63 (s, 2H), 1.60 (s, 4H).

EXAMPLE 3

N-[1(R)-[(1,2-Dihydro-1-methanesulfonylspiro[3H-indole-3,4'-piperdin]-1'-yl)carbonyl]-2-(phenylmethyloxy)ethyl]-2-amino-2-methylpropanamide mesylate This compound was prepared by the treating the free base obtained in Example 5, Step D, with methane sulfonic acid. The title compound was obtained by recrystallizing it from ethyl acetate-ethanol-water. m.p.=166°–168° C.

EXAMPLE 4

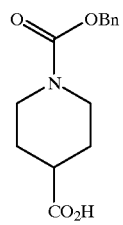

3

Isonipecotic acid-N-benzyl carbamate (3)

| Materials: | |
|---|---|
| Isonipecotic acid (2) T.C.I. | 4.02 kg (31.1 mol) |
| Benzyl chloroformate (Schweitzerhall) | 6.91 kg (40.5 mol) |
| K$_2$CO$_3$ | 10.1 kg (72.9 mol) |
| Water | 40.2 L |

Isonipecotic acid (2) and K$_2$CO$_3$ were dissolved in 40.2 L of water in a 100 L 4 neck flask with mechanical stirring under N$_2$ and the solution was cooled to 10° C. Benzyl chlorofornate was added, maintaining the temperature between 9 and 14° C., and the mixture was warmed up to 22° C. after the addition was complete and aged for 58 h. The addition was completed in 4 h at which point the pH was 9.0. After aging for 58 h there was no change in the pH.

The reaction mixture was transferred to a 200 L extractor and washed with 3×13 kg (15 L) of IPAC and 1×12 L of EtOAc. The aqueous layer was extracted with 8 L of toluene. After the washes the benzyl alcohol content was reduced from 3.8% to 1.4% by HPLC analysis. HPLC analytical: Dupont Zorbax 25 cm RXC8 column with 1.5 ml/min flow and detection at 254 nm; isocratic mixture with 35% MeCN, 65% of 0.1% aqueous H$_3$PO$_4$; retention times: 3=6.9 min, benzyl alcohol=3.3 min, toluene=17.3 min.

The aqueous phase was acidified with 37% aqueous HCl to pH 1.8. Carbon dioxide was evolved during the addition of HCl, but gas evolution was easily controlled. The addition of HCl took <1 h and required 10 L of conc. HCl. The aqueous phase was extracted with 3×6.6 L of toluene. The toluene extracts were dried with 2 kg of sodium sulfate and filtered through a pad of Solka-floc™. The combined filtrates weighed 17.8 kg. The crude yield of carbamate 3 was 7.89 kg (97%) (as obtained by evaporation of weighed aliquots of the filtrates to dryness). The filtrates were transferred through a 10μ inline filter to a 100 L flask. The extracts were concentrated at 10 mbar at <25° C. to a volume of 18 L. The final concentration of carbamate 3 was 440 g/L. The concentration of the toluene filtrate served to azeotropically remove final traces of water (final KF=170 mg/L). The product was 99.1 area % pure with 0.9 area % benzyl alcohol as the only impurity.

EXAMPLE 5

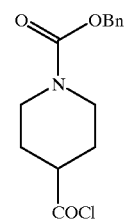

4

Isonipecotic acid chloride-N-benzyl carbamate (4)

| Materials: | |
|---|---|
| Isonipecotic acid N-benzyl carbamate in toluene. (MW = 263.30) | 7.89 kg (30.0 mol) in 17.9 L |
| Oxalyl chloride (MW = 126.93) | 3.94 kg (31.0 mol) |
| DMF (MW = 73.10) | 10 mL |
| Toluene | 12 L |

To the toluene solution of benzyl carbamate 3 from the preceding step was added 5 mL of DMF and 10 L of toluene. The oxalyl chloride was added over a period of 20 min. The reaction mixture was aged for 16 h at 18° C. under a slow stream of nitrogen. HPLC analysis of the reaction mixture showed that 1.3% of the carboxylic acid 3 still remained unreacted. The reaction mixture was warmed to 26° C., and 5 mL of DMF were added. The mixture was aged for 2.5 h. A 1.0 mL aliquot of the reaction mixture was quenched with 5.0 mL of tert-butylamine and analyzed after evaporation by HPLC: 25 cm Dupont Zorbax RXC8 column at 50° C. with 1 mL/min flow and detection at 220 nm; isocratic 42% MeCN, 58% of 0.1% aqueous H$_3$PO$_4$. This method showed that <0.05% of the acid 3 remained (as judged by A) and showed >3 area % B (>1 mol % (COCl)$_2$).

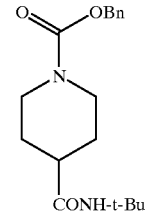

A

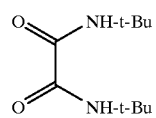

B

The mixture was concentrated at 10 mbar and a temperature of 20–25° C. until 5 L of solvent had been removed.

The typical HPLC profile of concentrated toluene solution after t-BuNH$_2$ quench described above is as follows:

| Retention time (min) | Area % | Identity |
|---|---|---|
| 2.1 | <0.5% | carboxylic acid 3 |
| 7.8 | <0.5% | benzyl chloride |
| 11.0 | >99% | Cbz-t-butylcarboxamide A |
| 12.1 | NA | toluene |
| 12.7 | <0.5% | ditert-butyloxamide B |

EXAMPLE 6

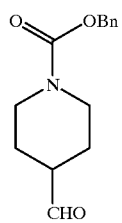

5

Piperidine-4-carboxaldehyde-1-benzyl carbamate (5)

| Materials: | |
|---|---|
| Isonipecotic acid chloride N-benzyl carbamate (4) in toluene (MW = 281.74) | 3.38 kg (12.0 mol) in 5.54 kg |
| DIEA (KF = 18 mg/L) | 1.55 kg (15.0 mol) |
| 10% Pd/C (KF <20 mg/g) | 101 g |
| thioanisole (MW = 124.21, d = 1.058) | 0.56 g |

The DIEA and thioanisole were added to the solution of (4) in toluene from the previous step and the catalyst was suspended in this mixture. The mixture was immediately placed into the 5 gal autoclave and hydrogenated at 20° C. and 40 psi of H$_2$. After 18 h the reaction had taken up 70% the theoretical amount of hydrogen and HPLC analysis of an aliquot that was quenched with tert-butylamine indicated that 14.2 area % of acid chloride 2 remained. HPLC conditions same as above. Retention time: 5=8.1 min.

A second charge of catalyst (101 g) and thioanisole (0.54 g) were added as a slurry in 1375 mL toluene to the hydrogenator. After 23 h HPLC analysis of an aliquot that was quenched with tert-butylamine indicated that 1.8 area % of acid chloride 2 remained. The mixture was purged with nitrogen and the catalyst and precipitated DIEA·HCl were removed by filtration through Solka-floc™. The filter cake was washed with 10 L of toluene. The filtrates were transferred through a 10μ inline filter to a 50 L extractor and washed with 2×7.2 L of 1 M aqueous HCl and 2×7.2 L of water. The mixture was concentrated at 10 mbar and a temperature of 25–30° C. until 5 L of residue remained.

| Retention time (min) | Area % | Identity |
|---|---|---|
| 2.1 | <2 | carboxylic acid 3 |
| 6.6 | <1 | dimer 21 |
| 8.1 | >95 | aldehyde 5 |

The assay yield of aldehyde 3 was 94% by HPLC analysis.

EXAMPLE 7

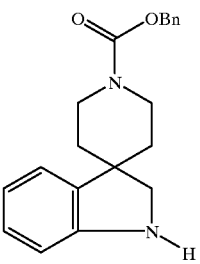

9

CBZ-Spiroindoline (9)

| Materials: | |
|---|---|
| Piperidine-4-carboxaldehyde-1-benzyl carbamate (5) in toluene solution | 1.71 kg (6.89 mol) in 21.4 kg |
| Phenylhydrazine | 900 mL, 981 g (9.15 mol) |
| Trifluoroacetic acid (TFA) | 2.20 L, 3.26 kg (28.6 mol) |
| NaBH$_4$ | 300 g, (7.93 mol) |
| Toluene | 34.4 kg |
| MeCN | 7.0 L |
| MeOH | 7.0 L |

The crude aldehyde 5 solution from the previous step was transferred through a 10μ inline filter to a 100 L reactor equipped with Teflon coated copper coils for cooling or heating and a mechanical stirrer. Toluene (34.4 kg) and MeCN (7 L) were added, and the resulting solution was cooled to 0° C. Phenylhydrazine was added in portions and the temperature was maintained at −1 to 3° C. while nitrogen was continuously bubbled through the reaction mixture.

The phenylhydrazine was added until TLC and HPLC analysis indicated complete consumption of the aldehyde 5 and the appearance of a slight excess (<5%) of phenylhydrazine. TLC conditions: Silica, E. Merck Kieselgel G60 F254 0.25 mm; diethyl ether/pentane (4/1); and developing agent 0.5% ceric sulfate, 14% ammonium molybdate in 10% aqueous sulfuric acid then heat; Rf: aldehyde 5=0.52, phenylhydrazone 7=0.61, phenylhydrazine 6=0.21.

HPLC conditions: 25 cm Dupont Zorbax RXC8 column at 30° C. with 1.0 mL/min flow and detection at 254 nm; gradient schedule:

| Time (min) | acetonitrile:water |
|---|---|
| 0 | 57:43 |
| 10 | 65:35 |
| 15 | 75:25 |
| 18 | 75:25 | retention times: phenylhydrazine 6=4.5 min, toluene=7.2 min, phenylhydrazone 7=11.4 min.

The reaction mixture was aged for 30 min at 0–2° C., and TFA was added maintaining the temperature between 2 and 7° C. The reaction mixture was warmed to 50° C. over 30 min, and maintained for 17 h. The nitrogen sparge through the reaction mixture was stopped and a slow stream of nitrogen was maintained over the reaction mixture. During the first hour at 5° C. the color gradually darkened to a deep green, and a relatively small amount of a white crystalline precipitate (ammonium trifluoroacetate) formed. After 17 h HPLC analysis (same conditions as above) indicated that the reaction mixture contained 91.6 area % indolenine 8 and 1.5% of unreacted phenylhydrazone remained. Aging the mixture for longer periods of time did not increase the assay yield of indolenine 8.

The reaction mixture was cooled to 12° C., and 7.0 L of MeOH was added. NaBH$_4$ was added in small (<20 g) portions maintaining the temperature below 15° C. The addition took 30 min. Moderate hydrogen evolution was observed during the addition, but it was easily controlled and there was virtually no frothing. Near the end of the addition the color rapidly changed from green to brown and then bright orange. A small amount (<200 mL) of a heavier phase had separated (presumably aqueous salts). HPLC analysis (conditions as before) indicated that all of the indolenine 8 had been consumed (90.4 area % CBZ-indoline 9); retention times: indolenine 8=7.5 min, indoline 9=8.2 min. TLC: ethyl ether as solvent, ceric sulfate-ammonium molybdate stain or 1% anisaldehyde stain; retention factors: indolenine 8=0.18, CBZ-indoline 9=0.33.

The color change from green to orange corresponds very closely to reaction end point. The quantity of NaBH$_4$ required to complete the reaction is heavily dependent on the temperature and rate of addition of NaBH$_4$, but the yield and quality of the product is virtually unaffected provided that the reaction is complete. The reaction mixture was cooled to 5° C. over a period of 30 min. Then 8 L of 3% aqueous NH$_4$OH (8 L) were added to bring the pH of the aqueous phase to 7.4, the mixture was agitated, and allowed to settle. The temperature rose to 15° C. The cloudy yellow lower aqueous phase was separated. The organic phase was washed with 4 L of 3% aqueous NH$_4$OH, 2×4 L of water, and 2×4 L of brine. The weight of the organic phase after the washings was 53.5 kg, and the assay yield was 94%.

The washed toluene solution was combined with the washed organic phases of two other similarly processed reactions. The total aldehyde used in the three reactions was 5.06 kg, (20.5 mol). The total weight of CBZ-indoline 9 assayed in the combined organic phases was 5.91 kg, (18.3 mol, 90% assay yield). The combined organic phases were dried with 5 kg of sodium sulfate, treated with 250 g of Darco G60 carbon for 30 min, and filtered through Solka-floc™. The filtrates were vacuum concentrated at 10 mbar at <25° C. until the residue was near dryness. The solvent switch was completed by slowly bleeding in 30 L of IPAC and reconcentrating to 14 L at 200 mbar at 50–60° C. The mixture was heated to reflux in order to obtain a clear homogeneous deep orange solution. $^1$H NMR analysis indicated that the solution contained ca. 6 mol % of residual toluene after solvent switch.

The solution was cooled to 68° C. and seeded with 4 g of crystalline CBZ-indoline 9. The solution was allowed to gradually cool to 26° C. over 6 h and aged for 9 h at 20–26° C. The slurry was cooled to 2° C. over 1 h and aged at 2° C. for 1 h. The product was isolated by filtration, and the filter cake was washed with 2×2 L of 5° C. IPAC and 2×2 L of 5° C. MTBE. The product was dried in the vacuum oven at 30° C. under a nitrogen bleed to give 4.37 kg (74%) of the title compound 9 as a light tan crystalline powder. HPLC analysis of the product indicated 99.5 area % purity. The mother liquor (11 L) and the washes contained 1.15 kg (19%) of additional product 9 and ca 3% of Cbz-isonipecotic acid phenylhydrazide (retention time=4.8 min).

EXAMPLE 8

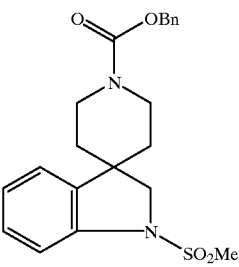

CBZ-Spiroindoline-methanesulfonamide (1)

| Materials: | |
|---|---|
| CBZ-Spiroindoline (9) | 1.69 kg (5.23 mol) |
| Methanesulfonyl chloride | 599 g (5.23 mol) |
| Et$_3$N (KF = 151) | 635 g (6.27 mol) |
| THF (KF = 41) | 12 L |

A 22 L flask was charged with the solid CBZ-spiroindoline 9 and then 11.5 L of THF and the Et$_3$N were transferred into the flask through a 10μ inline filter. The resulting homogenous solution was cooled to 0° C. A 1 L dropping funnel was charged with the methanesulfonyl chloride and 500 mL of THF. The solution of the MsCl in THF was added to the reaction mixture maintaining the temperature between 0 and 4° C. The addition took 5 h and was exothermic. A white precipitate, presumably triethylammonium hydrochloride formed during the addition. HPLC analysis indicated that the reaction was complete at the end of the addition (9 was undetectable.

HPLC conditions: 25 cm Dupont Zorbax RXC8 column with 1.5 mL/min flow and detection at 254 nm. Gradient Schedule:

| Time (min) | 0.1% aq. H$_3$PO$_4$:MeCN |
|---|---|
| 0 | 70:30 |
| 3 | 70:30 |
| 12 | 20:80 |
| 25 | 20:80 |

Retention times: 9=7.6 min, 1=13.6 min.

After the addition was complete the reaction mixture was warmed to 18° C. and aged for 16 h. There was no change in the appearance of the reaction mixture, and HPLC profile between the end of the addition and after the 16 h age. The reaction mixture was slowly transferred over 1 h into a vigorously stirred solution of 30 L of water and 200 mL of 37% aqueous HCl in a 50 L flask. The temperature in the 50 L flask rose from 22 to 28° C. The product separated as a pale tan gummy solid which changed to a granular solid. The aqueous suspension was cooled to 22° C. and aged for 1 h. The suspension was filtered, and the filter cake was washed with 2×4 L of MeOH/water (50/50). HPLC analysis indicated that <0.1% of the CBZ-Spiroindoline-methanesulfonamide1 was in the mother liquors.

The filter cake was washed with 4 L of MeOH/water (50/150) to which 50 mL of 28% aqueous NH$_4$OH had been added. The filter cake was washed with 2×4 L of MeOH/water (50/50), and the solid was dried in the vacuum oven

EXAMPLE 9

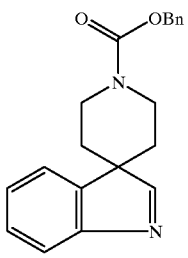

Optional Procedure for Isolation of Intermediate CBZ-Spiroindolenine (8)

Materials:

| | |
|---|---|
| Piperidine-4-carboxaldehyde-1-benzyl carbamate (5) | 12.37 g (0.050 mol) |
| Phenylhydrazine | 5.41 g (0.050 mol) |
| Trifluoroacetic acid (TFA) | 11.56 mL, 17.10 g (0.150 mol) |
| Methylene chloride | 500 mL |

The CBZ-aldehyde 5 was dissolved in dichloromethane in a 1 L flask equipped with Teflon coated magnetic stirring bar. The resulting solution was cooled to 0° C. Phenylhydrazine was added via a weighed syringe over 5 min and the temperature was maintained at −1 to 3° C. while nitrogen was continuously bubbled through the reaction mixture. TLC and HPLC analysis indicated complete consumption of the CBZ-aldehyde 5 and the appearance of a slight excess (<2%) of phenylhydrazine. TLC conditions: Silica, E. Merck Kieselgel G60 F254 0.25 mm; diethyl ether/pentane (4/1); and developing agent 0.5% ceric sulfate, 14% ammonium molybdate in 10% aqueous sulfuric acid then heat; Rf: aldehyde 5=0.52, phenylhydrazone 7=0.61, phenylhydrazine 6=0.21. HPLC conditions: 25 cm Dupont Zorbax RXC8 column at 30° C. with 1.0 mL/min flow and detection at 254 nm; gradient schedule:

| Time (min) | acetonitrile:water |
|---|---|
| 0 | 57:43 |
| 10 | 65:35 |
| 15 | 75:25 |
| 18 | 75:25 | retention times: phenylhydrazine 6=4.5 min, toluene=7.2 min. phenylhydrazone 7=11.4 min.

The reaction mixture was aged for 10 min at 0–2° C., and TFA was added by syringe maintaining the temperature between 2 and 7° C. The reaction mixture was warmed to 35° C. over 30 min, and maintained for 17 h. The nitrogen sparge through the reaction mixture was stopped and a slow stream of nitrogen was maintained over the reaction mixture. During the first hour at 35° C. the color gradually darkened to a rosy pink then to a deep green, and a relatively small amount of a white crystalline precipitate (ammonium trifluoroacetate) formed. After aging for 17 h HPLC analysis (same conditions as above) indicated that the reaction mixture contained 93 area % indolenine 8 and <0.5% of unreacted phenylhydrazone remained. Aging the mixture for longer periods of time did not increase the assay yield of indolenine 8. The reaction mixture was cooled to 10° C., and a mixture containing 60 mL 28–30% ammonium hydroxide, 90 mL water and 150 g crushed ice was added with good stirring. The color of the mixture changed to a salmon color. The organic phase was separated and washed twice with 400 mL water then 100 mL saturated aqueous NaCl. The organic phase was dried over magnesium sulfate and filtered through a plug of 5 g of silica. The filtrate was evaporated to give 15.84 g (99%) of indolenine 8 as a pale orange oil.

EXAMPLE 10

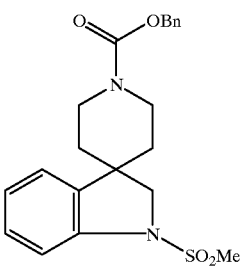

Procedure for the Preparation of CBZ-Spiroindoline-methanesulfonamide (1) without Isolation of Intermediate CBZ-Spiroindoline (9)

Step 1: CBZ-Spiroindoline (9)

Materials:

| | |
|---|---|
| Piperidine-4-carboxaldehyde-1-benzyl carbamate (5) | 49.5 g (0.20 mol) |
| Phenylhydrazine (Aldrich) | 23.7 g (0.22 mol) |
| Trifluoroacetic acid (TFA) | 75.4 g (0.66 mol) |
| Toluene (KF <250 mg/L) | 654 mL |
| MeCN (KF <250 mg/L) | 13.3 mL |
| $NaBH_4$ | 11.3 g, (0.30 mol) |
| Toluene | 20 mL |
| MeOH | 50 mL |

A 2% (by volume) solution of MeCN in toluene was made up using 654 mL of toluene and 13.3 mL of MeCN. In a 2 L 3 neck flask equipped with a mechanical stirrer 617 ml of the above solution were degassed by passing a fine stream of nitrogen through the solution for 5 min. Phenylhydrazine and TFA were added to the mixture while still degassing.

The CBZ-aldehyde 5 was dissolved in the rest of the solution prepared above (50 mL) and degassed by bubbling nitrogen through the solution while in the addition funnel. The solution in the flask was heated to 35° C., and the aldehyde solution was slowly added to the phenylhydrazine-TFA over 2 h. The mixture was aged at 35° C. for 16 h.

HPLC conditions: 25 cm Dupont Zorbax RXC8 column at 50° C. with 1 mL/min flow and detection at 220 nm; isocratic 55% MeCN, 45% of 0.1% aqueous $H_3PO_4$. Typical HPLC profile after 16 h age:

| Retention time (min) | Area % | Identity |
| --- | --- | --- |
| 1.6 | 0.1–0.5 | phenylhydrazine 6 |
| 4.1 | <0.1 | dimer 21 |
| 4.7 | <0.1 | aldehyde 5 |
| 5.0 | NA | spiroindoline 9 |
| 6.3 | NA | toluene |
| 6.9 | 97 | spiroindolenine 8 |
| 10.3 | <0.2 | phenylhydrazone 7 |
|  | 2–3 tot. | other impurities <0.2% ea. |

The mixture was cooled to −10° C. and MeOH was added. A suspension of sodium borohydride in 20 mL toluene was added in small portions (1 mL) over 30 min taking care that the temperature did not exceed −2° C.

| Area % | Identity |
| --- | --- |
| 0.1–1 | phenylhydrazine 6 |
| 85–90 | CBZ-spiroindoline 9 |
| <0.1 | CBZ-spiroindolenine 8 |
| 10–15 tot. | other impurities (<3% ea.) |

The temperature was raised to 10° C. over 1 h, and 6% aqueous ammonia (200 mL) was added. The mixture was agitated for 10 min, allowed to settle for another 10 min, and the lower aqueous phase was drawn off. Acetonitrile (20 mL) and MeOH (20 mL) were added to the organic phase and it was washed with 150 mL of 15% brine. The organic phase was found to contain a 92% assay yield of CBZ-spiroindoline 9.

Step 2: CBZ-Spiroindoline-methanesulfonamide (1)

| Materials: |  |
| --- | --- |
| CBZ-Spiroindoline (9) (MW = 322.51) | (0.184 mol) |
| Methanesulfonyl chloride | 21.1 g (0.18.4 mol) |
| DIEA (KF = 150 mg/L) | 29.7 g, 40.1 mL (0.230 mol) |
| THF (KF = 41 mg/L) | 150 mL |

The crude solution of CBZ-spiroindoline 9 solution from Step 1 above was concentrated in a 1 L 3 neck flask (60–70° C., 150–200 Torr) until 250 g of residue remained. The THF and DIEA were added, and the resulting homogenous solution was cooled to 0° C. A 125 mL dropping funnel was charged with the methanesulfonyl chloride and 50 mL of THF. The solution of MsCl in THF was added over 2 h to the reaction mixture maintaining the temperature between 0 and 4° C. and the mixture was aged for 2 h at 5–8° C. The addition was slightly exothermic. A white precipitate, presumably DIEA-hydrochloride, formed during the addition. HPLC conditions were the same as above. HPLC analysis indicated that the reaction was complete 1 h after the end of the addition (9 was undetectable) and the assay yield was 94% from 9. Retention time: 1=7.8 min. Typical HPLC profile of reaction mixture after 2 h age:

| Area % | Identity |
| --- | --- |
| <0.1 | CBZ-spiroindoline 9 |
| 90–92 | CBZ-sulfonamide 1 |
| 8–10 tot. | other impurities (<2% ea.) |

The mixture was warmed to 20° C., and 200 mL of 1M aqueous HCl was added. The mixture was warmed to 50° C., and the aqueous phase was separated. The organic phase was washed sequentialy with 100 mL water, 100 mL 5% aqueous sodium bicarbonate, and 100 mL water. The organic phase was transferred to a 1 L 3 neck flask equipped for mechanical stirring and distillation. The mixture (ca 400 mL) was distilled at atmospheric pressure until 150 mL of distillate had been collected. The head temperature reached 107° C.; the pot temperature was 110° C. The distillation was continued with continuous addition of n-propanol at such a rate as to maintain a constant volume (ca 350 mL) in the pot. The distillation was stopped when a total of 525 mL of n-PrOH had been added and a total of 800 mL of distillate had been collected.

The temperature of both the head and pot rose from 94° C. to 98° C. during the solvent switch. Toluene and n-PrOH form an azeotrope boiling at 97.2° C. composed of 47.5% toluene and 52.5% n-PrOH. The mixture was allowed to cool gradually to 20° C. over 3 h and aged for 12 h. The mother liquor was found to contain 2% toluene and 4 mg/mL of sulfonamide. The solubility of the sulfonamide in various mixtures of toluene and n-PrOH has been determined by HPLC assay:

| % toluene in n-PrOH | solubility of 1 in mg/mL |
| --- | --- |
| 0 | 2.36 |
| 5 | 3.02 |
| 10 | 4.23 |
| 20 | 7.51 |
| 25 | 10.3 |

The crystalline slurry was filtered and washed with 3×100 mL of n-PrOH. The product was dried in a vacuum oven at 50° C. with a nitrogen bleed for 16 h to furnish 65.5 g (82% from aldehyde 5) of 6 as a tan solid with 93.5 wt % purity. Typical HPLC profile of solid:

| Area % | Identity |
| --- | --- |
| <0.1 | CBZ-spiroindoline 9 |
| >99 | CBZ-sulfonamide 1 |
| <1 tot. | other impurities (<0.2% ea.) |

For additional purification, a 40.0 g sample of the n-PrOH crystallized sulfonamide was dissolved in 134 mL of EtOAc at 60° C. and treated with 8.0 g of Darco G-60 carbon for 1 h at 60° C. After the addition of 2.0 g Solkafloc™, the slurry was filtered through a pad of 4.0 g Solkafloc™, and the pad was washed with 90 mL of EtOAc at 60° C. Prior to the addition of the carbon the solution was a brown color. The filtration proceeded well without plugging to give a golden yellow filtrate. The filtrate was distilled at atmospheric pressure in a 500 mL flask (pot temperature 80–85° C.) until 100 g (100 mL) of residue remained. This solution was allowed to cool to 35° C. over 3 h. Over a 1 h period, 116 mL of cyclohexane was added with good agitation at 35° C. The mixture was cooled to 20° C. over 1 h and aged at 20° C. for 12 h. At 35° C. much of the sulfonamide has crystallized out and the mixture was thick. Addition of cyclohexane at 20° C. makes agitation difficult. After the aging period, the supernatant was found to contain 2.5 mg 1/g. The crystalline slurry was filtered and the cake was washed with 77 mL of 2:1 cyclohexane-EtOAc and 2×77 mL of cyclohexane. The product was dried in a vacuum oven at 50° C. with a nitrogen bleed for 16 h to furnish 34.2 g of 1 (MW=400.3) as a white crystalline solid (85% recovery from crude 1, 70% from 5 with >99.9 wt % purity).

EXAMPLE 11

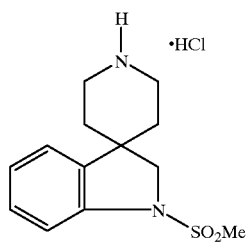

1a

HCl Salt of Spiroindoline-methanesulfonamide (1a)

Materials:

| | |
|---|---|
| CBZ-spiroindoline-methanesulfonamide (1) | 941 g (2.35 mol) |
| Pearlman's catalyst 20% Pd(OH)$_2$/C | 188 g |
| THF | 8 L |
| MeOH | 7 L |

The catalyst was suspended in 7 L of MeOH and transferred into the 5 gal autoclave followed by the solution of 1 in 8 L of THF.

The mixture was hydrogenolyzed at 25° C. at 80 psi of H$_2$. After 2.5 h the temperature was raised to 35° C. over 30 min.

HPLC analysis indicated complete consumption of Cbz-spiroindoline-methanesulfonamide. HPLC conditions: 25 cm Dupont Zorbax RXC8 column with 1.5 mL/min flow and detection at 254 nm. Gradient Schedule:

| Time (min) | 0.1% aq. H$_3$PO$_4$:MeCN |
|---|---|
| 0 | 70:30 |
| 3 | 70:30 |
| 12 | 20:80 |
| 25 | 20:80 | retention times: Spiroindoline = 7.6 min, Cbz-spiroindoline-methanesulfonamide = 13.6 min.

The mixture was purged with nitrogen and the catalyst was removed by filtration through Solka-floc™ while still warm. The catalyst was washed with 4 L of THF and 2 L of MeOH. The pale yellow filtrates were concentrated to a thick oil at 10 mbar and <25° C. The solvent switch was completed by slowly bleeding in 15 L of EtOAc and reconcentrating to dryness. The residue solidified to a hard off-white mass. MeOH (1.5 L) was added and the mixture was heated to 70° C. to give a homogenous solution. While the solution was at 70° C., 10.5 L of EtOAc at 20° C. was added. The temperature fell to 40° C., and the mixture remained homogenous.

Subsequent experiments suggested that it is more convenient to solvent switch the MeOH-THF filtrates to. MeOH, concentrate to the desired volume, and then add the EtOAc. This avoids the solidification of the residue upon concentration of the EtOAc solution.

Hydrogen chloride diluted with about an equal volume of nitrogen was passed into the solution. The temperature rose to 60° C. over the course of 15 min, and a white precipitate of the hydrochloride salt formed. Diluting the HCl with nitrogen only avoids the reaction mixture sucking back and may not be necessary.

The mixture was cooled in an ice bath, and the hydrogen chloride addition was continued for 1 h. The temperature gradually fell to 20° C. The suspension was aged for 2 h while the temperature was lowered to 10IC. The crystalline product was isolated by filtration, and the filter cake was washed with 3 L of EtOAc. It was dried in the vacuum oven at 35° C. to give 1.18 kg (86%) of the title product 1 a as an off-white crystalline solid of >99.5 area % purity by HPLC analysis. HPLC conditions: 25 cm Dupont Zorbax RXC8 column with 1.5 mL/min flow and detection at 230 nm; isocratic 35% MeCN, 65% of 0.1% aqueous ammonium acetate. Retention time: 1a=5.4 min.

EXAMPLE 12

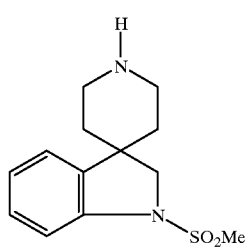

1b

Spiroindoline-methanesulfonamide (Free base form) (1b)

A 250 mL aliquot of the filtrate from the Cbz-hydrogenolysis containing 4.67 g of 1b (free base) was concentrated to ca 10 mL. The residue was dissolved in 20 mL of EtOAc and the solution was reconcentrated to ca 10 mL. This was repeated once more, and 10 mL of EtOAc was added to the residue. A crystalline precipitate began to form. MTBE (20 mL) was added in one portion. Additional crystalline solid precipitated, but the supernatent still contained a substantial quantity of dissolved product which did not precipitate on standing. Hexanes (70 mL) were added dropwise over 2 h to the mixture with vigorous stirring. The slow addition of the hexanes is neccessary to avoid the oiling out of the amine. The agitated mixture was aged for 1 h and filtered. The filter cake was washed with 20 mL of 1:1 MTBE-hexanes and then with 20 mL of hexanes. The product was dried under a stream of nitrogen to give 3.86 g (82%) of the free amine of 1b as an off white crystalline solid of >99.5 area % purity. HPLC conditions: 25 cm Dupont Zorbax RXC8 column with 1.5 mL/min flow and detection at 230 nm; isocratic 35% MeCN, 65% of 0.1% aqueous ammonium acetate. Retention time: 1b=5.4 min.

EXAMPLE 13A

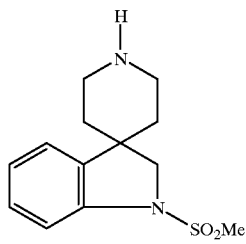

Spiroindoline-methanesulfonamide (Free base form) (1b)

| Materials: | |
|---|---|
| CBZ-Spiroindoline-sulfonamide (1) | 833.5 g (2.08 mol) |
| Pd(OH)$_2$/C (20% weight of Pd(OH)$_2$) | 124.5 (15%) |
| THF | 6.5 L |
| MeOH | 19.5 L |
| NH$_4$OH (conc) | 60 mL |

The hydrogenation was run three (3) times due to equipment limitations; this procedure refers to a single run. The CBZ spiroindoline sulfonamide1 was dissolved in THF (6.5 L, KF=53 μg/μL) and then MeOH (KF=18 μg/mL, 4 L) was added followed by addition of the catalyst and the slurry was transferred to a 5 gal autoclave. The remainder of the MeOH (2.5 L) was used for rinsing. The mixture was heated to 40° C. at 50 psi for 24 hours. The catalyst loading and reaction time are a function of the purity of starting material 1. This material was unique requiring ≧15% catalyst and long reaction time. Purer batches of spiroindoline required only 5% of catalyst and 4–6 hrs reaction time.

Upon completion (<0.1 A % 1 by LC) the mixture was filtered thru Solka Floc™ and the carbon cake washed with MeOH (13 L) containing NH$_4$OH (0.5%, 60 mL). The combined filtrates (assay shows 1587 g of spiroindoline amine 1b) were concentrated in vacuo and the resulting solids were partitioned between 40 L (of toluene:THF (3:1) and 0.5N NaOH (18 L). Although the layers separated easily a heavy precipitate could be seen in the aqueous layer. The aqueous suspension was thus extracted with CH$_2$Cl$_2$ (15 L). The aqueous and organic layer separated slowly. Prior to CH$_2$Cl$_2$ addition THF was added to the aqueous layer along with enough NaCl to saturate the layer. However dissolution of the product was not achieved which necessitated the use of CH$_2$Cl$_2$.

The combined toluene, THF and CH$_2$Cl$_2$ layers were combined and concentrated in the batch concentrator. The residue was flushed with 7 L of CH$_3$CN. Finally 10 L of CH$_3$CN were added and the solution stood overnight under N$_2$ atmosphere.

EXAMPLE 13B

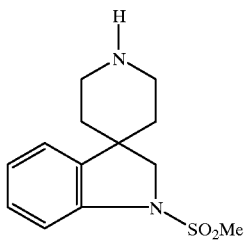

Spiroindoline-methanesulfonamide (Free base form) (1b)

| Materials: | |
|---|---|
| CBZ-Spiroindoline-sulfonamide (1) | 3 kg (7.49 mol) |
| Darco G-60 | 600 g |
| Ethyl Acetate | 36 L |
| Absolute Ethanol | 189 L |
| 10% Pd/C | 450 g |
| Ammonia Solution | 500 ml |
| Solka Floc ™ | 2.5 kg |
| Isopropyl Acetate | 65 L |

A mixture of CBZ-spiroindoline (1) (1 kg) and Darco G-60 (200 g) in ethyl acetate (9 L) was stirred and heated at 60–65° C. under a nitrogen atmosphere for 8 hours. The Darco was removed by filtration at 60–65° C., the solid washed with hot ethyl acetate (3 L) and the filtrate and washings combined. LC wt/wt assay confirmed negligible loss to the Darco. The ethyl acetate solution was evaporated to dryness in vacuo using a 20 L Buchi apparatus and then flushed with absolute ethanol (2×5 L). This material was then slurried in absolute ethanol (8 L) warmed to 65–70° C. and placed in the 20 L autoclave. The batch was rinsed in with absolute ethanol (1 L). A slurry of 10% Palladium on charcoal (75 g, 7.5% by weight) in absolute ethanol (750 ml) was then added to the autoclave and rinsed in with a further portion of absolute ethanol (250 ml).

The batch was hydrogenated at 65° C. with vigorous stirring under 40 psi hydrogen pressure for 3 hours, a second portion of 10% palladium on charcoal (75 g) was added, the batch was hydrogenated for a further 2 hours and then sealed overnight. The batch was transferred (still hot, 60–65° C.) to a 20 L Buchi apparatus and degassed in vacuo to remove formic acid by "feeding and bleeding" absolute ethanol (18 L total).

This procedure was repeated twice more and the three batches were combined in a 10 gallon glass-lined vessel and the combined batch was degassed again by the addition and distillation (in vacuo) of absolute ethanol (2×10 L). Solka floc™ (0.5 kg) was added to the batch and rinsed in with ethanol (10 L). An Estrella filter was loaded with Solkafloc™ (2 kg) as a slurry in ethanol (20 L). The resulting mixture was warmed to 60–65° C. and then transferred at this temperature via heated filter using pump to two tared stainless-steel bins. The initial vessel, the filter, the pump and the lines were rinsed with a hot (60–65° C.) mixture of aqueous ammonia (500 ml) in absolute ethanol (25 L). The filtrate and washings were combined in the two stainless-steel bins.

The batch was then transferred to a vessel using an in-line filter containing a 10 micron cartridge, and then concentrated in vacuo to low bulk (~15 L). The ethanol was replaced by isopropyl acetate by the "feeding and bleeding" of 3x batch volumes of isopropyl acetate (45 L total), while maintaining a batch volume of ~15 L. The solvent switch, when complete, contained <1% residual ethanol by GC. The batch was then diluted to ~33 L by the addition of isopropyl acetate (20 L), and this solution of spiroindoline-amine 1b (1.855 kg by LC analysis) in isopropyl acetate was used for the next stage of the process.

EXAMPLE 14A

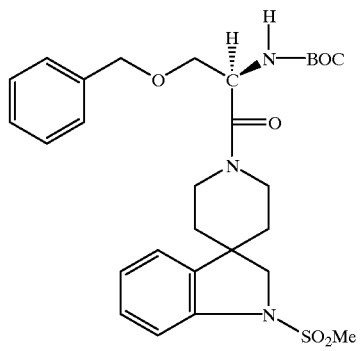

Boc-O-Benzylserine Spiroindoline (11)

| Materials: | |
|---|---|
| Spiroindoline-amine (1b) | 1587 g (5.966 moles) |
| Amino acid (10) | 1938 g (6.563 moles) |
| 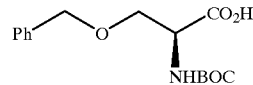 | |
| DCC | 1334.5 g (6.563 moles) |
| HOBT | 884 g (6.563 moles) |
| CH$_3$CN | 25 L |
| 0.5N NaOH | 18 L |
| 0.5N HCl | 18 L |
| NaHCO$_3$ sat. | 18 L |
| iPrOAc | 28 L |

The spiroindoline-amine1b in CH$_3$CN or iPrOAc:H$_2$O (25 L) at ambient temperature under N$_2$ was treated in sequence with HOBT (884 g; 1.1 eq) as a solid, DCC (1334.5 g, 1.1 eq) as the melt (heating in hot water at 60° C. for ca. 1 hr) and finally the amino acid 10 (1938 g) as the solid. The mixture was stirred for 3 hr upon which time heavy precipitation of DCU occurred and LC analysis showed ca. 0.5 A % of amine 1b remaining. IPAc (9 L) was added, the slurry was filtered through Solka Floc™ and the cake was washed with IPAc (19 L). The combined organic solution was washed in sequence with 0.5N NaOH (18 L), 0.5N HCl (18 L) and saturated NaHCO$_3$ (18 L). A final water wash at this point resulted in an emulsion and was thus eliminated.

The organic layer was concentrated in vacuo and the residue was dissolved in MeOH or EtOH (10 L final volume). Assay yield 3026 gr (89%).

The use of alternative peptide coupling agents such as carbonyldiimidazole or formation of mixed anhydrides, such as sec-butyl carbonate, gave inferior yields of 11 and/or 14 with a high degree of epimerization in the case of the former compound. Other peptide coupling reagents were prohibitively expensive.

EXAMPLE 14B

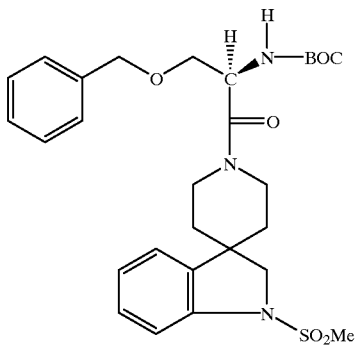

Boc-O-Benzylserine Spiroindoline (11)

| Materials: | |
|---|---|
| Spiroindoline-amine (1b) | 1.855 kg (6.96 mol) |
| Isopropyl acetate | 29 L |
| Dicyclohexylcarbodiimide (DCC) | 1.58 kg (7.65 mol) |
| 1-Hydroxybenzotriazole (HOBt) | 1.03 kg (7.62 mol) |
| N-Boc-O-benzyl-D-Serine | 2.26 kg (7.65 mol) |
| 1 M Aqueous sodium hydroxide | 26 L |
| 0.5 M Aqueous hydrochloric acid | 26 L |
| Satd. Aqueous sodium hydrogen carbonate | 26 L |
| Absolute Ethanol | 50 L |

Water (20 L) was added to a stirred solution of the spiroindoline-amine1b (1.855 kg) in isopropyl acetate (33 L) in a reaction vessel. The following chemicals were then added sequentially at room temperature under a nitrogen atmosphere: DCC (1.58 kg, 1.1 equivs.), HOBt (1.03 kg, 1.1. equivs.) and finally N-Boc-O-benzyl-D-Serine (2.26 kg, 1.1 equivs.). The reagents were rinsed in with isopropyl acetate (7 L). The batch was stirred at room temperature under nitrogen atmosphere for 5 hours when LC showed the ratio of product/starting material to be 99.4/0.6. The mixture was then filtered through an Estrella filter using cloth and cardboard only and utilizing a pump into another vessel. The sending vessel was rinsed with isopropyl acetate (22 L) and this was used to rinse the filter, the pump and the lines into the receiving vessel. The 2-phase mixture in the vessel was stirred for 10 minutes and then allowed to settle for 15 minutes. The lower aqueous layer was separated off and the organic solution was left to stand at room temperature overnight.

The next day, the organic solution was washed with 1M aqueous sodium hydroxide solution (26 L) then 0.5M aqueous hydrochloric acid (26 L) and finally saturated aqueous sodium hydrogen carbonate (26 L). LC analysis gave an assay yield of 3.787 kg, 93% overall yield from 7.49 moles (3 kg) of starting CBZ-spiroindoline (1). The batch was concentrated in vacuo (internal temperature=13–15° C. jacket temperature=40° C., Vacuum=29") to low bulk (~15 L) and solvent switched to ethanol by "feeding and bleeding" ethanol (50 L) whilst maintaining the volume at ~15 L. GC showed <1% isopropyl acetate remaining. This solution was used for the next stage of the process.

EXAMPLE 15A

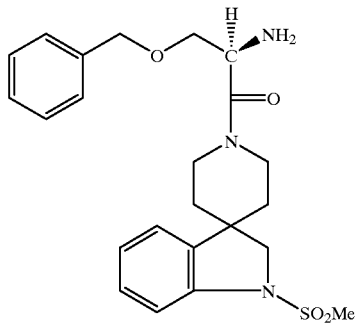

O-Benzylserine Spiroindoline (free base form) (12)

| Materials: | |
|---|---|
| Boc-O-Benzylserine Spiroindoline (11) | 3026 g (5.57 moles) |
| Methane sulfonic acid (MsOH) | 1.16 L (17.9 moles) |
| MeOH | 10 L |
| iPrOAc | 24 L |
| 0.5 N NaOH | 35 L |

The Boc-O-benzylserine spiroindoline 11 in 10 L of MeOH (or EtOH) was treated with neat MsOH (1.16 L) added over ca. 30–40 min, (initial temperature 16° C., final temperature 28° C.). The dark red solution was aged overnight under $N_2$. The mixture was then pumped into a 100 L extractor containing 24 L iPrOAc and 35 L 0.5 N NaOH. The pH of the aqueous layer was 7. NaOH (6M) was added until pH ≧10.5. As the pH increased the color changed from red to yellow. The layers were separated and the organic layer (24 L) was shown by NMR to contain 13 mole % of MeOH in iPrOAc [5 volume %]. LC assay 2.48 kg.

EXAMPLE 15B

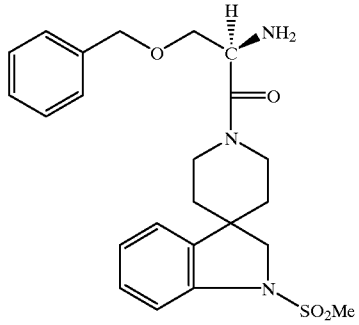

O-Benzylserine Spiroindoline (free base form) (12)

| Materials: | |
|---|---|
| Boc-O-Benzylserine Spiroindoline (11) | 3.787 kg (6.96 mol) |
| Methanesulphonic acid | 2.006 kg (20.87 mol) |
| Isopropyl acetate | 38 L |

| -continued | |
|---|---|
| Materials: | |
| 1 M Aqueous sodium hydroxide | 16 L |
| 50% Aqueous sodium hydroxide | 1.6 L |

Methanesulphonic acid (2.006 kg, 1.355 L, ~3 equivs.) was added to the stirred solution of Boc-O-benzylserine spiroindoline (11) (3.787 kg) in ethanol (total volume -15 L) in a reaction vessel. The batch was warmed to 35–40° C. After 7 hours, LC showed the absence of starting material and the reaction was allowed to cool to room temperature overnight. The next day, water (44 L) was added to the batch with stirring. The batch was cooled to ~5°, stirred for 30 minutes and then filtered through an in-line filter (loaded with a 10μ cartridge) into a bin. The batch was then sucked back into the vessel. A water rinse (10 L) was used to rinse the vessel and lines into the bin and this was used to then rinse back into the vessel. Isopropyl acetate (38 L) was added followed by a 1M aqueous sodium hydroxide (16 L). The batch was cooled to 10–15° C., the pH of the lower aqueous layer was confirmed as ~7 and 50% aqueous sodium hydroxide solution was added (1.6 L) (pH>10). The batch was stirred at 10–15° C. for 25 minutes and then allowed to settle for 10–15 minutes. The lower aqueous layer was separated (78.1 kg). LC assay indicated 28.4 g of 12 (0.85% of theory) contained in the aqueous liquors. Volume of the organic solution=51 L. LC assay indicated 3.057 kg, 92% overall yield from 3 kg, 7.49 moles of CBZ-spiroindoline sulfonamide (1). This solution was used for the next stage.

EXAMPLE 16A

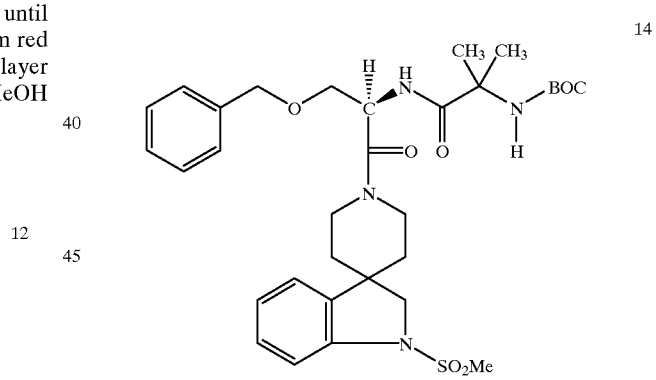

Boc-Aminoisobutyryl O-Benzylserine Spiroindoline (14)

| Materials: | |
|---|---|
| Spiroindoline amine (12) | 2481 g (5.57 moles) |
| amino acid peptide (13) | 1247.1 g (6.16 moles) |
| DCC | 1266.7 g (6.16 moles) |
| HOBT | 827 g (6.16 moles) |
| IPAc | 52 L |

-continued

| Materials: | |
|---|---|
| H₂O | 37 L |
| 0.5N NaOH | 36 L |
| 0.5N HCl | 36 L |
| Sat. NaHCO₃ | 36 L |

The solution of the amine 12 in IPAc was diluted to a total volume of 39 L with IPAc and 37 L of H₂O was added. The biphasic mixture was then treated in sequence with HOBT (827 g) as a solid, DCC (1266.7 g) as a melt, and amino acid 13 at ambient temperature under nitrogen. The reaction mixture was stirred for 2 h upon which time LC analysis indicated dissappearance of the starting material 12 (<0.3 A %). The mixture was filtered through Solka Floc™ and the solids were washed with 13 L of IPAc. The material may be stored at this point as a biphasic mixture overnight.

The mixture was transferred to a 100 L extractor, the aqueous layer was separated and the organic layer was washed successively with 36 L of 0.5N NaOH, 0.5N HCl and saturated NaHCO₃. Assay yield 3160 g (81% from spiroindoline ±5% for volume measurement error). The solution was concentrated to a small volume and was flushed with ethanol (2×4 L). If desired, the inermediate compound 14 may be isolated by adding water to crystalize it out.

The use of alternative peptide coupling agents such as carbonyldumidazole or formation of mixed anhydrides, such as sec-butyl carbonate, gave inferior yields of 14 with a high degree of epimerization. Other peptide coupling reagents were prohibitively expensive.

EXAMPLE 16B

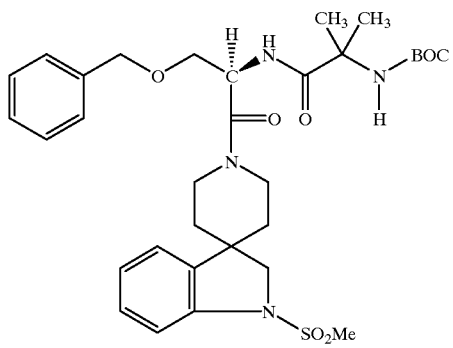

Boc-Aminoisobutyryl O-Benzylserine Spiroindoline (14)

| Materials: | |
|---|---|
| Spiroindoline amine (12) | 3.057 kg (6.89 mol) |
| Dicyclohexylcarbodiimide (DCC) | 1.56 kg (7.56 mol) |
| 1-Hydroxybenzotriazole (HOBt) | 1.02 kg (7.55 mol) |
| Boc-2-Aminoisobutyric acid (13) | 1.54 kg (7.58 mol) |
| Isopropyl acetate | 32 L |
| 1 M Aqueous sodium hydroxide | 38 L |
| 0.5 M Aqueous hydrochloric acid | 38 L |
| Satd. aqueous sodium hydrogen carbonate | 38 L |
| Absolute ethanol | 45 L |

Water (49 L) was added to the stirred solution of the spiroindoline amine 12 (3.057 kg) in isopropyl acetate (total volume ~51 L) in a reaction vessel at room temperature under a nitrogen atmosphere. The following chemicals were then added sequentially: DCC (156 kg, ~1.1 equivs.), HOBt (1.02 kg, ~1.1 equivs.) and finally, N-Boc-2-aminoisobutyric acid 13 (1.54 kg, ~1.1 equivs.). The mixture was stirred vigorously at room temperature for 2 hours when LC showed the reaction to be complete. The mixture was filtered to to another vessel via an Estrella filter using a pump. Isopropyl acetate (22 L) was used to rinse vessel, the filter, the pump and the lines into the receiving vessel. The 2-phase mixture was then stirred for 5 minutes and the layers were allowed to separate. The lower aqueous layer was separated without incident (weight of aqueous liquors=51.1 kg). The organic solution was then washed sequentially with 1M aqueous sodium hydroxide (38 L), 0.5M aqueous hydrochloric acid (38 L) and finally, saturated aqueous sodium hydrogen carbonate (38 L) without incident.

The organic solution was then transferred using a pump via an in-line filter (containing a 10μ cartridge) to another vessel for the solvent switch to ethanol. The vessel was rinsed with isopropyl acetate (10 L) and this was used to rinse the pump, the filter and the lines into the receiving vessel. The filtrate and washings were combined. Total volume=75 L (by dipstick). LC assay gave 4.395 kg of Boc-aminoisobutyryl O-benzylserine spiroindoline (14), i.e. 93% overall from 7.49 moles of starting CBZ-spiroindoline sulfonamide (1).

The batch was concentrated in vacuo to low bulk (-15 L) and the isopropyl acetate switched to ethanol by "feeding and bleeding" absolute ethanol (45 L total). At the end of the solvent switch, GC showed <1% isopropyl acetate remaining. This solution (25 L) containing 4.395 kg of 14 was used for the next stage. If desired, the inermediate compound 14 may be isolated by adding water to crystalize it out.

EXAMPLE 17A

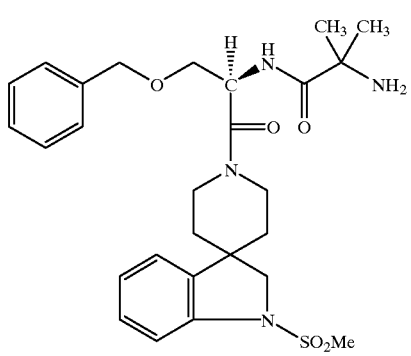

Aminoisobutyryl O-Benzylserine Spiroindoline (15)

| Materials: | |
|---|---|
| Boc Spiroindoline (14) | 3160 g (5.03 moles) |
| Methanesulfonic acid (MsOH) | 979 mL (15.1 moles) |
| EtOH | 6.2 L |
| H₂O | 30 L |
| 1N NaOH | 11 L |
| EtOAc | 26 L |
| Darco 60 activated carbon | 1 Kg |

The Boc spiroindoline 14 was dissolved in 6.2 L of EtOH and treated with MsOH (979 mL). The temperature rose from 20 to 30° C. and the reaction was allowed to proceed overnight. After 12 hours at 20° C. there was still 15 A % of starting material left so the mixture was heated to 35° C. for 6 hours. Upon completion (<0.1 A % 14) the reaction was cooled to 200° C. and 30 L of H₂O were added and the solution was filtered through a glass funnel with a polypropylene filter to filter off residual DCU. The mixture was transferred to a 100 L extractor and 26 L of EtOAc were added. The aqueous layer was basified via addition of chilled 1N NaOH (11 L) and 1 L of 50% NaOH. Addition of ice was required to keep the temperature below 14° C. Higher temperatures resulted in significant emulsion problems.

The organic layer was distilled at 50° C. at ca. 21" of Hg until KF<1000 μg/mL. Lower KF's result in more efficient carbon treatments and better recovery at the salt formation step. KF's of 160 μg/mL were achieved at the 700 g scale. The solution was diluted with ethyl acetate to a total volume of 31 L (LC assay 2.40 kg). Activated carbon (Darco G-60) was added and the mixture was stirred for 24 h. The mixture was filtered through Solka Floc™ and the filter cake was washed with ethyl acetate (16 L), assay 2.34 Kg.

EXAMPLE 17B

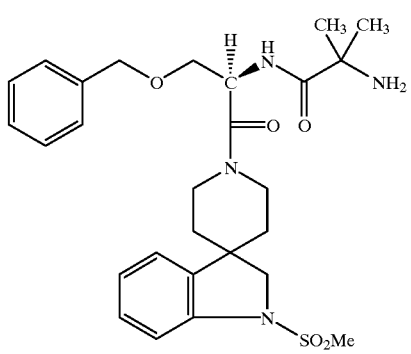

Aminoisobutyryl O-Benzylserine Spiroindoline (15)

| Materials: | |
|---|---|
| Boc Spiroindoline (14) | 4.395 kg (6.99 mol) |
| Methanesulfonic acid | 2.017 kg (20.99 mol) |
| Ethyl acetate | 185 L |
| 1 M Aqueous sodium hydroxide | 16 L |
| 50% Aqueous sodium hydroxide | 2.6 L |
| Darco G-60 | 900 g |
| Solka Floc ™ | 2.5 kg |

Methanesulfonic acid (2.017 kg, 1.36 L, ~3 equivs.) was added to the stirred solution of the Boc spiroindoline 14 (4.395 kg) in ethanol (total volume ~25 L) in a reaction vessel at room temperature. The batch was warmed to 35–40° C., and stirred overnight. On the next day, the batch contained ~1.1 A % of starting material and so the reaction was continued for a further 4 hours, then LC showed ratio of product/starting material to be 99.6/0.4. The batch was concentrated in vacuo to ~15 L volume and then diluted with water (44 L). The batch was cooled to 5° C., stirred for 30 minutes and then filtered through a Sparkler in-line filter (containing a 10μ cartridge) using a pump to another vessel to remove a small amount of residual DCU.

The vessel, the pump, the filter and the lines were rinsed with water (10 L), and this was added to the vessel. Ethyl acetate (36 L) was added to the vessel and the stirred mixture was cooled to 10° C. A solution of cold (5–10° C.) 1M aqueous sodium hydroxide solution (16 L) and cold (5–10° C.) 50% aqueous sodium hydroxide solution (2.6 L) were added at 10° C. and the temperature rose to 14° C. The resulting mixture was stirred for 15 minutes at <14° C. and then the lower aqueous layer separated off.

The batch was concentrated in vacuo to ~20 L volume and then a mixture of ethyl acetate (35 L) and ethanol (5 L) was fed in while maintaining the volume at ~20 L. At the end of this distillation the KF was 9160 mgml⁻¹. The batch was solvent switched to ethyl acetate by "feeding and bleeding" ethyl acetate (40 L total). At the end of this distillation, KF was 446 mgml⁻¹. The batch was diluted with ethyl acetate (10 L).

Darco G-60 (900 g) was added to the hazy mixture. This was rinsed in with ethyl acetate (6 L). This mixture was stirred at room temperature overnight. Next day, Solka Floc™ (0.5 kg) was added to the stirred batch in the vessel and then Solka Floc™ (2.0 kg) was stirred in a little ethyl acetate and loaded into an Estrella filter. The excess solvent was pumped away through a Sparkler in-line filter containing a 10μ cartridge. The slurry was transferred from the vessel through a filter using a pump and then through another filter to 2×40 L stainless steel bins. Visual inspection showed the liquors to be clear and clean. The vessel was rinsed with ethyl acetate (22 L) and this was used to rinse through the route outlined above to the stainless steel cans. The contents of both cans was transferred into a reaction vessel and the solution was mixed thoroughly.

The batch (58 L) had a KF of 2950 mgml⁻¹ and so was redried by concentrating in vacuo to 20–25 L volume. The batch was diluted to 46 L volume (dipstick) by the addition of ethyl acetate (25 L). The KF was 363 mgml⁻¹. The batch was diluted to 62 L volume by the addition of ethyl acetate (17 L) and was used for the final stage of the process.

EXAMPLE 18A

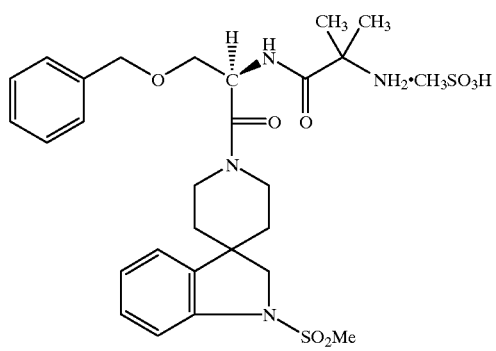

Spiro[3H-indole-3,4'-piperdin]-1'-yl)carbonyl]-2-(phenylmethyl-oxy)ethyl]-2-amino-2-methylpropanamide Methanesulfonate (16)

| Materials: | |
|---|---|
| Amine (15) | 2340 g (4.43 moles) |
| Methane sulfonic acid (MsOH) | 316 mL (4.88 moles) |
| EtOAc | 60 L |

-continued

| Materials: | |
|---|---|
| EtOH | 4.8 L |
| 8% EtOH in EtOAc | 20 L |

The volume of the solution of 15 from the previous step was adjusted to 60 L with ethyl acetate and EtOH (4.8 L) was added. The MsOH (316 mL) was added in 3 L of EtOAc at 45° C. To the deep red homogeneous solution was added 496 g of the title compound Form I seed (10% seed based on the weight of the free amine was employed). The temperature rose to ca. 48° C. and the reaction was aged at 52° C. for 1.5 hours. Analysis indicated complete conversion to the title compound (Form I). (At less than 10% seed longer age (>3 hours) was required). The slurry was allowed to cool to 20° C. overnight and was filtered in a centrifuge under $N_2$. The cake was washed with 20 L of 8% EtOH in EtOAc. $N_2$ is essential during filtration because the wet crystals are very hygroscopic. The batch was dried at 35° C. under vacuum to afford 2.7Kg (56% overall yield) of the title compound (Form I) (99.9 A % purity; <0.1% enantiomer).

The conversion of Form II to Form I is also accomplished where the salt is formed in EtOAc-EtOH by addition of MsOH as above and the initial solution of the salt (at 55° C.) is cooled to 45° C. Crystals start appearing at that temperature and the slurry becomes thicker with time. The temperature is then raised to 51° C. and the slurry is aged overnight. Complete conversion to Form I of 16 should be expected. This procedure may also be employed to prepare seed crystals of Form I of 16.

EXAMPLE 18B

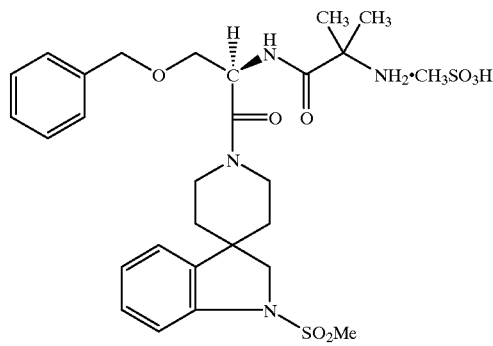

Spiro[3H-indole-3,4'-piperdin]-1'-yl)carbonyl]-2-(phenylmethyl-oxy)ethyl]-2-amino-2-methylpropanamide Methanesulfonate (16)

| Materials: | |
|---|---|
| Amine (15) | 3.1 kg (5.86 mol) |
| Methanesulfonic acid | 620 g (6.45 mol) |
| Ethyl acetate | 37 L |
| Absolute ethanol | 8.7 L |
| Spiro[3H-indole-3,4'-piperdin]-1'-yl)-carbonyl)-2-(phenylmethyl-oxy)ethyl]-2-amino-2-methylpropanamide methanesulfonate (Form I) | 70 g (0.11 mol) |

Absolute ethanol (6.4 L) was added to the solution of the amine (15) (3.1 kg) in ethyl acetate (total volume ~62 L) in a reacttion vessel. The batch was warmed to 50° C. and a solution of methanesulfonic acid (620 g, 412 ml, 1.1 equivs.) in ethyl acetate (11 L) was added over ~5 minutes at 50–54° C. The batch was seeded with spiro[3H-indole-3,4'-piperdin]-1'-yl)-carbonyl]-2-(phenylmethyl-oxy)ethyl]-2-amino-2-methylpropanamide methanesulfonate (Form I) (70 g) and the resulting slurry was stirred and heated at 55° C. under nitrogen atmosphere overnight.

The next day, the slurry was cooled to 15–20° C., held for 2 hours and then dropped to the 50 cm polypropylene filter under nitrogen atmosphere. The solid product was washed with a mixture of absolute ethanol (2.3 L) in ethyl acetate (26 L). The white, solid product was dug off and dried in an Apex oven in vacuo at 35° C. for an appropriate time (approx. two days). The dried spiro[3H-indole-3,4'-piperdin]-1'-yl)-carbonyl]-2-(phenylmethyl-oxy)ethyl]-2-amino-2-methylpropanamide methanesulfonate (3.352 kg) was sieved using a Jackson-Crockatt sieve to give 3.347 kg (including seed, 70 g)} yield=3.277 kg.

HPLC Conditions:
LC Retention times on Zorbax RX-C8 (4.6 mm×25 cm), $\lambda$=210 nm, flow rate=1.5 ml/min.
Compound 1: 60:40 $CH_3CN—H_2O$ (1% $H_3PO_4$) RT=5.0 min
Compound 1b: 35:65 $CH_3CN—H_2O$ (0.1 w % $NH_4OAc$) RT=6.2 min.
Compound 10: 60:40 $CH_3CN—H_2O$ (0.1 $H_3PO_4$) RT=2.9 min.
Compound 11: 60:40 $CH_3CN—H_2O$ (0.1% $H_3PO_4$) RT=5.4 min.
Compound 12: 40:60 $CH_3CN—H_2O$ [pH 5.25 $NaH_2PO4$ (6.9 g/L of $H_2O$) (adjust pH with NaOH)] RT=5.6 min
Compound 14: 60:40% $CH_3CN—H_2O$ (0.1% $H_3PO_4$) RT=4.65 min
Compound 15: 40:60% $CH_3CN—H_2O$ [pH=5.25 $NaH_2PO4$ (6.9 g/L of $H_2O$)] adjust pH with NaOH)RT=4.9 min
LC Retention times on Zorbax RX-C8 (4.6 mm×25 cm), $\lambda$=210 nm, flow rate=1.2 ml/min, column temperature=48° C.
Solvent A=0.05% Phosphoric acid+0.01% Triethylamine in water
Solvent B=Acetonitrile
Gradient system:

| Time | % A | % B |
|---|---|---|
| 0 min | 95 | 5 |
| 35 min | 10 | 90 |
| 38 min | 95 | 5 |
| 40 min | 95 | 5 |

| | Retention time (mins) |
|---|---|
| Compound 1 | 25.2 |
| Compound 1b | 8.5 |
| Compound 10 | 20.5 |
| Compound 11 | 26.3 |
| Compound 12 | 14.8 |
| Compound 14 | 25.6 |
| Compound 15 | 15.7 |

EXAMPLE 19

Procedure for Manufacturing 1.0 mg Potency Tablets of N-[1(R)-[(1,2-dihydro-1-methanesulfonylspiro[3H-indole- 3,4'-piperdin]-1'-yl)carbonyl]-2-(phenylmethyloxy)ethyl]-2-amino-2-methylpropanamide methanesulfonate

| Ingredient | Per Tablet | Per 2600 Tablets |
|---|---|---|
| Active ingredient (N-[1(R)-[(1,2-dihydro-1-methane-sulfonylspiro[3H-indole-3,4'-piperdin]-1'-yl)carbonyl]-2-(phenylmethyloxy)-ethyl]-2-amino-2-methyl-propanamide methanesulfonate) | 1.18 mg | 3.068 g |
| Calcium Phosphate Dibasic | 47.32 mg | 123.03 g |
| Starch Pregelatinized NF 1500 | 30.00 mg | 78.0 g |
| Microcrystalline Cellulose NF Avicel PH 101 | 15.00 mg | 39.0 g |
| Magnesium Stearate Impalpable Powder NF | 0.50 mg | 1.3 g |
| Croscarmellose Sodium NF | 12.75 mg | 33.15 g |
| Ethanol 95% | 7.5 µl | 19.5 ml |
| Water purified (Tablet Weight = 100 g) | 22.5 µl | 58.5 ml |

The active ingredient (equivalent to 1.0 mg anhydrous free base per tablet) was mixed with the calcium phosphate dibasic, the starch pregelatinized NF 1000, the microcrystalline cellulose NF, and half of the croscarmellose sodium NF in a high shear granulator for 5 minutes. The 25% ethanol/water granulating solution was slowly added to the powder mixture with the mixer running over a period of about 1.5 minutes then granulated for about 7 minutes to form granules. The wet granules were dried at about 47° C. (range 46 to 48° C.) in a tray dryer or a fluid bed dryer for approximately 3.0 hours. The dried granules were then milled using a Quadro Comill to achieve fine granules. After milling, the remainder of the croscarmellose sodium NFS was added to the fine granules and mixed in a V blender for about 10 minutes. Magnesium stearate impalpable powder NF was added to this blend through a 60 mesh stainless steel screen and blended in the V blender for about 1 minute. The lubricated mixture was compressed to provide tablets of 1.0 mg active ingredient (free base equivalent).

EXAMPLE 20
Procedure for Manufacturing 1.0 mg Potency Coated Tablets of N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide methanesulfonate

| Ingredient | Per Tablet | Per 2600 Tablets |
|---|---|---|
| Hydroxypropyl Methylcellulose USP (HPMC) | 0.80 mg | 2.08 g |
| Hydroxypropyl Cellulose NF with <0.3% Silica (HPC) | 0.80 mg | 2.08 g |
| Titanium Dioxide USP | 0.32 mg | 0.83 g |
| Talc USP Purified | 0.08 mg | 0.21 g |
| Water Purified (Film Coated Tablet Weight = 102 g) | To 20 µl | To 52 ml |

The titanium dioxide and talc, USP were mixed and passed through a 60 mesh stainless steel screen. This mixture was mixed with HPMC and HPC to form a dry blend. The dry blend was added to water (20 ml) which was previously heated to 90° C. with mild agitation to ensure that the blend is wetted to form a slurry. The remainder of the water (up to 32 ml) was added to the slurry at ambient temperature with gentle agitation to form a suspension. The suspension was then applied to the tablets from the previous Example using the following guidelines to provide the coated tablets.

Pan: suitable size
Pan Speed: 20 RPM
Nozzles: 2850 liquid/120 air
Inlet Temperature: 85° C.
Bed Temperature: 47° C.
Spray Rate: ca. 2.0 g/minute/kg Tablets EXAMPLE 21
Procedure for Manufacturing 5.0 mg Potency Tablets of N-[1(R)][(1,2-dihydro-1-methanesulfonylspiro[3H-indole-3,4'-piperdin]-1'-yl)carbonyl]-2-(phenylmethyloxy)ethyl]-2-amino-2-methylpropanamide methanesulfonate

| Ingredient | Per Tablet | Per 25,000 Tablets |
|---|---|---|
| Active Ingredient (N-[1(R)-[1,2-dihydro-1-methane-sulfonylspiro-[3H-indole-3,4'-piperdin]-1'-yl)-carbonyl]-2-(phenylmethyloxy)-ethyl]-2-amino-2-methylpropan-amide methanesulfonate) | 5.91 mg | 147.8 g |
| Calcium Phosphate Dibasic | 188.10 mg | 4.70 kg |
| Starch Pregelatinized NF 1500 | 120.00 mg | 3.00 kg |
| Microcrystalline Cellulose NF Avicel PH 101 | 60.00 mg | 1.50 kg |
| Magnesium Stearate Impalpable Powder NF | 2.00 mg | 50.0 g |
| Croscarmellose Sodium NF | 24.00 mg | 600 g |
| Ethanol 95% | 30 µl | 750 ml |
| Water purified (Tablet Weight = 400 g) | 90 µl | 2.25 l |

The active ingredient (equivalent to 5.0 mg anhydrous free base per tablet) was mixed with the calcium phosphate dibasic, the starch pregelatinized NF 1000, the microcrystalline cellulose NF, and half of the croscarmellose sodium NF in a high Fielder 10/25 mixer for about 6 minutes. The 25% ethanol/water granulating solution was slowly added to the powder mixture with the mixer running over a period of about 1.5 minutes then granulated for about 8 minutes to form granules. The wet granules were dried at about 47° C. (range 46 to 48° C.) in a tray dryer or a fluid bed dryer for approximately 3.0 hours. The dried granules were then milled using a Quadro Comill to achieve fine granules. After milling, the remainder of the croscarmellose sodium NFS was added to the fine granules and mixed in a V blender for about 10 minutes. Magnesium stearate impalpable powder NF was added to this blend through a 60 mesh stainless steel screen and blended in the V blender for about 1 minute. The lubricated mixture was compressed to provide tablets of 5.0 mg active ingredient (free base equivalent).

EXAMPLE 22
Procedure for Manufacturing 5.0 mg Potency Coated Tablets of N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide methanesulfonate

| Ingredient | Per Tablet | Per 25,000 Tablets |
|---|---|---|
| Hydroxypropyl Methylcellulose USP (HPMC) | 3.2 mg | 80 g |
| Hydroxypropyl Cellulose NF with <0.3% Sillca (HPC) | 3.2 mg | 80.0 g |
| Titanium Dioxide USP | 1.28 mg | 32.0 g |
| Talc USP Purified | 0.32 mg | 8.0 g |

-continued

| Ingredient | Per Tablet | Per 25,000 Tablets |
|---|---|---|
| Water Purified (Film Coated Tablet Weight = 408 g) | To 80 µl | To 200 ml |

Using essentially the procedure of the prior Example 20 and applying the suspension to the tablets from the previous Example, 5.0 mg potency coated tablets were formed.

EXAMPLE 23
Procedure for Manufacturing 25 mg Potency Tablets of N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide methanesulfonate

| Ingredient | Per Tablet | Per 25,000 Tablets |
|---|---|---|
| Active Ingredient (N-[1(R)-[(1,2-dihydro-1-methane-sulfonylspiro-[3H-indole-3,4'-piperdin]-1'-yl)-carbonyl]-2-(phenylmethyloxy)-ethyl]-2-amino-2-methylpropanamide methanesulfonate) | 29.55 mg | 738.75 g |
| Calcium Phosphate Dibasic | 174.46 mg | 4.361 kg |
| Starch Pregelatinized NF 1500 | 113.00 mg | 2.825 kg |
| Microcrystalline Cellulose NF Avicel PH 101 | 57.00 mg | 1.425 kg |
| Magnesium Stearate Impalpable Powder NF | 2.00 mg | 50.0 g |
| Croscarmellose Sodium NF | 24.00 mg | 600 g |
| Ethanol 95% | 30 µl | 750 ml |
| Water purified (Tablet Weight = 400 g) | 90 µl | 2.25 l |

The active ingredient (equivalent to 25 mg anhydrous free base per tablet) was mixed with the calcium phosphate dibasic, the starch pregelatinized NF 1500, the microcrystalline cellulose NF, and half of the croscarmellose sodium NF in a high shear granulator Fielder 10/25 mixer for about 6 minutes. The 25% ethanol/water granulating solution was slowly added to the powder mixture with the mixer running over a period of about 1.5 minutes then granulated for about 8 minutes to form granules. The wet granules were dried at about 47° C. (range 46 to 48° C.) in a tray dryer or a fluid bed dryer for approximately 3.0 hours. The dried granules were then milled using a Quadro Comill to achieve fine granules. After milling, the remainder of the croscarmellose sodium NFS was added to the fine granules and mixed in a V blender for about 10 minutes. Magnesium stearate impalpable powder NF was added to this blend through a 60 mesh stainless steel screen and blended in the V blender for about 1 minute. The lubricated mixture was compressed to provide tablets of 25 mg active ingredient (free base equivalent).

EXAMPLE 24
Procedure for Manufacturing 25 mg Potency Coated Tablets of N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide methanesulfonate

| Ingredient | Per Tablet | Per 25,000 Tablets |
|---|---|---|
| Hydroxypropyl Methylcellulose USP (HPMC) | 3.2 mg | 80 g |
| Hydroxypropyl Cellulose NF with <0.3% Silica (HPC) | 3.2 mg | 80.0 g |
| Titanium Dioxide USP | 1.28 mg | 32.0 g |
| Talc USP Purified | 0.32 mg | 8.0 g |
| Water Purified (Film Coated Tablet Weight = 408 g) | To 80 µl | To 200 ml |

Using essentially the procedure of Example 20 and applying the suspension to the tablets from the previous Example, 25 mg potency coated tablets were formed.

EXAMPLE 25
Procedure for Manufacturing 100 mg Potency Tablets of N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide methanesulfonate

| Ingredient | Per Tablet | Per 2600 Tablets |
|---|---|---|
| Active Ingredient (N-[1(R)-[(1,2-dihydro-1-methane-sulfonylspiro[3H-indole-3,4'-piperdin]-1'-yl)-carbonyl]-2-(phenylmethoxyloxy)-ethyl]-2-amino-2-methylpropanamide methane-sulfonate) | 118.20 mg | 307.3 g |
| Calcium Phosphate Dibasic | 81.80 mg | 212.7 g |
| Starch Pregelatinized NF 1500 | 78.00 mg | 202.8 g |
| Microcrystalline Cellulose NF Avicel PH 101 | 60.00 mg | 156.0 g |
| Magnesium Stearate Impalpable Powder NF | 2.00 mg | 5.20 g |
| Croscarmellose Sodium NF | 60.00 mg | 156.0 g |
| Ethanol 95% | 30.0 µl | 78.0 ml |
| Water purified (Tablet Weight = 400 g) | 90.0 µl | 234.0 ml |

The active ingredient (equivalent to 100 mg anhydrous free base per tablet) was mixed with the calcium phosphate dibasic, the starch pregelatinized NF 1000, the microcrystalline cellulose NF, and half of the croscarmellose sodium NF in a high shear granulator for 5 minutes. The 25% ethanol/water granulating solution was slowly added to the powder mixture with the mixer running over a period of about 1.5 minutes then granulated for about 7 minutes to form granules. The wet granules were dried at about 47° C. (range 46 to 48° C.) in a tray dryer or a fluid bed dryer for approximately 3.0 hours. The dried granules were then milled using a Quadro Comill to achieve fine granules. After milling, the remainder of the croscarmellose sodium NFS was added to the fine granules and mixed in a V blender for about 10 minutes. Magnesium stearate impalpable powder NF was added to this blend through a 60 mesh stainless steel screen and blended in the V blender for about 1 minute. The lubricated mixture was compressed to provide tablets of 100 mg active ingredient (free base equivalent).

EXAMPLE 26
Procedure for Manufacturing 100 mg Potency Coated Tablets of N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide methanesulfonate

| Ingredient | Per Tablet | Per 2600 Tablets |
|---|---|---|
| Hydroxypropyl Methylcellulose USP (HPMC) | 3.2 mg | 8.32 g |
| Hydroxypropyl Cellulose NF with <0.3% Silica (HPC) | 3.2 mg | 8.32 g |
| Titanium Dioxide USP | 1.28 mg | 3.33 g |
| Talc USP Purified | 0.32 mg | 0.83 g |
| Water Purified (Film Coated Tablet Weight = 408 g) | To 80.0 µl | To 208 ml |

Using essentially the procedure of Example 20 and applying the suspension to the tablets from the previous Example, 100 mg potency coated tablets were formed.

EXAMPLE 27
Preparation of amorphous form of N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide methanesulfonate As a mimic of the tablet formulation process, a concentrated solution of N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide methanesulfonate (118 mg) in 120 µL 25% aqueous ethanol (980 mg/ml) was evaporated at 40° C. to give a solid. The lack of crystallinity was confirmed by X-ray analysis. The X-ray diffraction pattern showed an amorphous halo. Examination of the solid under microscopy showed no biorefringence.

The solid state chemical stability of the amorphous form was studied after 12 weeks at 40° C., 60° C. and 80° C., and it was found to exhibit excellent stability. After 12 weeks at 40° C., 100% of the initial compound was present; after 12 weeks at 60° C., 99.7% of the initial compound was present; after 12 weeks at 80° C., 97.8% of the initial compound was present.

EXAMPLE 28
Chemical Stability of Film Coated Tablets of N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide methanesulfonate Following 6.0 Months Stability Study The results of a 6.0 month stability study of film coated tablets of N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide methanesulfonate are presented below.

| Stability Chamber | % of initial 1.0 mg dose | % of initial 100 mg dose |
|---|---|---|
| 30° C./Amient Humidity | 99 | 99 |
| 30° C./75% Relative Humidity | 99 | 99 |
| 40° C./75% Relative Humidity | 99 | 99 |

In particular, no degradates were observed for the 100 mg dose. Degradates were observed for the 1.0 mg dose varying from 0.1 to 0.7 area % relative to active only at 40° C./75% relative humidity. Furthermore, the tablet dissolution, disintegration, and hardness for both the 1.0 mg dose and the 100 mg dose were satisfactory following 6.0 months storage under the above conditions.

EXAMPLE 29
Tablet Crushing Strength and Disintegration Times of 100 mg Potency Tablets of N-[1(R)-[(1,2-dihydro-1-methanesulfonylspiro [3H-indole-3,4'-piperdin]-1'-yl)carbonyl]-2-(phenylmethyloxy)ethyl]-2-amino-2-methylpropanamide methanesulfonate Tablets of 400 mg compression weight were prepared by the procedures of the above examples using 118.2 mg of N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide methanesulfonate per tablet (29.6% tablet weight). All granulations were prepared on a several gram scale by pestle and morter using 25% ethanol/75% water as a granulating solution. Tablets were compressed on a Carver Press under 1000 lb force (uncoated tablet cores), unless otherwise noted.

Formulation A: wet granulation—Starch Pregelatinized NF 1500 (34.8%); Microcrystalline Cellulose NF Avicel PH 101 (34.8%); Talc USP (0.6%); Magnesium Stearate (0.3%).

Formulation B: direct compression—Calcium Phosphate Dibasic (26.3%); Microcrystalline Cellulose NF Avicel PH 102 (39%); Talc USP (1.2%); Magnesium Stearate (0.6%); Croscarmellose Sodium NF (3%).

Formulation C: wet granulation, compressed under 500 lb force—Starch Pregelatinized NF 1500 (33.3%); Microcrystalline Cellulose NF Avicel PH 101 (33.3%); Talc USP (0.6%); Magnesium Stearate (0.3%); Croscarmellose Sodium NF (3%=1.5% intragranular+1.5% extragranular).

Formulation D: wet granulation—Starch Pregelatinized NF 1500 (33.3%); Microcrystalline Cellulose NF Avicel PH 101 (33.3%); Talc USP (0.6%); Magnesium Stearate (0.3%); Croscarmellose Sodium NF (3% extragranular).

Formulation E: wet granulation—Microcrystalline Cellulose NF Avicel PH 101 (36.4%); Calcium Phosphate (26.3%); Talc USP (1.2%); Magnesium Stearate (0.6%); Croscarmellose Sodium NF (6%=3% intragranular+3% extragranular).

Formulation F: wet granulation—Microcrystalline Cellulose NF Avicel PH 101 (15.0%); Calcium Phosphate (29.5%); Starch Pregelatinized NF 1500 (19.5%); Magnesium Stearate (0.5%); Croscarmellose Sodium NF (6%=3% intragranular+3% extragranular).

Formulation G: wet granulation—Microcrystalline Cellulose NF Avicel PH 101 (15.0%); Calcium Phosphate (26.5%); Starch Pregelatinized NF 1500 (19.5%); Magnesium Stearate (0.5%); Croscarmellose Sodium NF (9%=3% intragranular+6% extragranular).

Formulation H: wet granulation—Microcrystalline Cellulose NF Avicel PH 101 (15.0%); Calcium Phosphate (26.5%); Starch Pregelatinized NF 1500 (19.5%); Magnesium Stearate (0.5%); Croscarmellose Sodium NF (9%=3% intragranular+6% extragranular); Super Disintegrant (12% extragranular).

| Formulation | Tablet Hardness (kP) | Disintegration Time (min) |
|---|---|---|
| A | Does not break | 13.0 |
| B | 23.3 (one tablet) | 7.0 |
| C | 23.7 (one tablet) | 14.0 |
| D | 29.2 ± 1.2 (three tablets) | 13.5 ± 0.25 |
| E | 14.1 ± 0.7 (three tablets) | 12.5 ± 1.6 |
| F | 13.5 ± 1.1 (three tablets) | 20.5 ± 0.0 |
| G | 18.5 (two tablets) | 14.0 |
| H | 14.9 (two tablets) | 7.5 |

As demonstrated above, the present formulations have superior properties regarding strength and stability. The tablet hardness is suitable for film coating and disintegration time is not too long.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compound of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A pharmaceutical composition comprising:
   0.1 to 50% by weight of an active ingredient N-[1(R)-[(1,2-dihydro-1-methanesulfonylspiro[3H-indole-3,4'-piperdin]-1'-yl)carbonyl]-2-(phenylmethyloxy)ethyl]-2-amino-2-methyl-propanamide, or a pharmaceutically acceptable salt thereof;
   20 to 40% by weight of a binder/diluent which is selected from: hydroxypropyl methylcellulose, hydroxypropyl cellulose, pregelatinized starch and polyvinylpyrrolidone;
   10 to 20% by weight of a first diluent which is selected from: lactose, microcrystalline cellulose, calcium phosphate dibasic, mannitol, powdered cellulose and pregelatinized starch;
   20 to 50% by weight of a second diluent which is selected from: lactose, microcrystalline cellulose, calcium phosphate dibasic, mannitol, powdered cellulose and pregelatinized starch;
   5 to 15% by weight of a disintegrant which is selected from microcrystalline or croscarmellose sodium; and
   0.05 to 5% by weight of a lubricant which is selected from magnesium stearate, calcium stearate, and steric acid;
   wherein sum of the above proportions of the active ingredient, the binder/diluent, the first diluent, the second diluent, the disintegrant, and the lubricant are not greater than 100% by weight.

2. A pharmaceutical composition comprising:
   about 1 to 30% by weight of an active ingredient N-[1-(R)-[(1,2-dihydro-1-methanesulfonylspiro[3H-indole-3,4'-piperdin]-1'-yl)carbonyl]-2-(phenylmethyloxy)ethyl]-2-amino-2-methyl-propanamide, or a pharmaceutically acceptable salt thereof;
   about 20 to 40% by weight of pregelatinized starch;
   about 10 to 20% by weight of microcrystalline cellulose;
   about 20 to 50% by weight of calcium phosphate dibasic;
   about 5 to 15% by weight of croscarmellose sodium; and
   about 0.05 to 5% by weight of magnesium stearate,
   wherein the sum of the above proportions of active ingredient, pregelatinized starch, microcrystalline cellulose, calcium phosphate dibasic, croscarmellose sodium, and magnesium stearate are not greater than 100% by weight.

3. The pharmaceutical composition of claim 2 comprising: about 1 to 2% by weight of the active ingredient; about 25 to 35% by weight of pregelatinized starch; about 10 to 20% by weight of microcrystalline cellulose; about 45 to 55% by weight of calcium phosphate dibasic; about 4 to 8% by weight of croscarmellose sodium; and about 0.1 to 1% by weight of magnesium stearate wherein the sum of the above proportions of active ingredient, pregelatinized starch, microcrystalline cellulose, calcium phosphate dibasic, croscarmellose sodium, and magnesium stearate are not greater than 100% by weight.

4. The pharmaceutical composition of claim 3 comprising: about 1.18% by weight of the active ingredient which is N-[1(R)-[(1,2-dihydro-1-methane-sulfonylspiro [3H-indole-3,4'-piperdin]-1'-yl)carbonyl]-2-(phenylmethyloxy)ethyl]-2-amino-2-methyl-propanamide methanesulfonate; about 30.0% by weight of pregelatinized starch; about 15.0% by weight of microcrystalline cellulose; about 47.3% by weight of calcium phosphate dibasic; about 6.0% by weight of croscarmellose sodium; and about 0.5% by weight of magnesium stearate.

5. The pharmaceutical composition of claim 4 further comprising a coating of about 0.8% by weight of hydroxypropyl methylcellulose; about 0.8% by weight of hydroxypropyl cellulose; about 0.32% by weight of titanium dioxide; and about 0.08% by weight of talc (as a percentage of the core tablet weight).

6. The pharmaceutical composition of claim 3 comprising: about 1.48% by weight of the active ingredient which is N-[1(R)-[(1,2-dihydro-1-methane-sulfonylspiro[3H-indole-3,4'-piperdin]-1'-yl)carbonyl]-2-(phenylmethyl-oxy)ethyl]-2-amino-2-methyl-propanamide methanesulfonate; about 30.0% by weight of pregelatinized starch; about 15.0% by weight of microcrystalline cellulose; about 47.0% by weight of calcium phosphate dibasic; about 6.0% by weight of croscarmellose sodium; and about 0.5% by weight of magnesium stearate.

7. The pharmaceutical composition of claim 6 further comprising a coating of about 0.8% by weight of hydroxypropyl methylcellulose; about 0.8% by weight of hydroxypropyl cellulose; about 0.32% by weight of titanium dioxide; and about 0.08% by weight of talc (as a percentage of the core tablet weight).

8. The pharmaceutical composition of claim 2 comprising: about 5 to 10% by weight of the active ingredient, about 25 to 35% by weight of pregelatinized starch; about 10 to 20% by weight of microcrystalline cellulose; about 40 to 50% by weight of calcium phosphate dibasic; about 4 to 8% by weight of croscarmellose sodium; and about 0.1 to 1% by weight of magnesium stearate, wherein the sum of the above proportions of the active ingredient, pregelatinized starch, microcrystalline cellulose, calcium phosphate dibasic, croscarmellose sodium, and magnesium stearate are not greater than 100% by weight.

9. The pharmaceutical composition of claim 8 comprising: about 7.39% by weight of the active ingredient which is N-[1(R)-[(1,2-dihydro-1-methane-sulfonylspiro[3H-indole-3,4'-piperdin]-1'-yl)carbonyl]-2-(phenylmethyl-oxy)ethyl]-2-amino-2-methyl-propanamide methanesulfonate; about 28.2% by weight of pregelatinized starch; about 14.2% by weight of microcrystalline cellulose; about 43.6% by weight of calcium phosphate dibasic; about 6.0% by weight of croscarmellose sodium; and about 0.5% by weight of magnesium stearate.

10. The pharmaceutical composition of claim 9 further comprising a coating of about 0.8% by weight of hydroxypropyl methylcellulose; about 0.8% by weight of hydroxypropyl cellulose; about 0.32% by weight of titanium dioxide; and about 0.08% by weight of talc (as a percentage of the core tablet weight).

11. The pharmaceutical composition of claim 2 comprising: about 25 to 35% by weight of the active ingredient, about 15 to 25% by weight of pregelatinized starch; about 10 to 20% by weight of microcrystalline cellulose; about 15–25% by weight of calcium phosphate dibasic; about 10 to 20% by weight of croscarmellose sodium; and about 0.1 to 1% by weight of magnesium stearate, wherein the sum of the above proportions of the active ingredient, pregelatinized starch, microcrystalline cellulose, calcium phosphate dibasic, croscarmellose sodium, and magnesium stearate are not greater than 100% by weight.

12. The pharmaceutical composition of claim 11 comprising: about 29.5% by weight of the active ingredient which is N-[1(R)-[(1,2-dihydro-1-methane-sulfonylspiro[3H-indole-3,4'-piperdin]-1'-yl)carbonyl]-2-(phenylmethyl-oxy)ethyl]-2-amino-2-methyl-propanamide methanesulfonate; about 19.5% by weight of pregelatinized starch; about 15.0% by weight of microcrystalline cellulose; about 20.4% by weight of calcium phosphate dibasic; about 15.0% by weight of croscarmellose sodium; and about 0.5% by weight of magnesium stearate.

13. The pharmaceutical composition of claim 12 further comprising a coating of about 0.8% by weight of hydroxypropyl methylcellulose; about 0.8% by weight of hydroxypropyl cellulose; about 0.32% by weight of titanium dioxide; and about 0.08% by weight of talc (as a percentage of the core tablet weight).

14. A process for the preparation of a tablet containing an active ingredient of the compound: N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide, or a pharmaceutically acceptable salt thereof, comprising the steps of:

(1) forming a powder blend of the active ingredient with a binder/diluent, a first diluent, a second diluent, and a first portion of a disintegrant, (2) wet granulating the powder blend with a solution of ethanol/water to form granules, (3) drying the granules to remove the ethanol/water, (4) adding a second portion of a disintegrant;

(5) lubricating the granules; and (6) compressing the dried granules into a desired tablet form.

15. The process of claim 14 wherein the active ingredient is N-[1(R)-[(1,2-dihydro-1-methanesulfonylspiro[3H-indole-3,4'-piperdin]-1'-yl)carbonyl]-2-(phenylmethyloxy)ethyl]-2-amino-2-methyl-propanamide methanesulfonate.

16. The process of claim 14 further comprising coating the tablet by:

(1) dry blending titanium dioxide with hydroxypropyl methylcellulose and hydroxypropyl cellulose to form a dry powdered blend;

(2) adding the dry powdered blend to water to form a slurry;

(3) adding water to the slurry with stirring to form a suspension; and (4) applying the suspension to the tablets.

17. The process of claim 14, comprising the steps of:

(1) forming a powder blend of the active ingredient with a binder/diluent, a first diluent, a second diluent, and a disintegrant, from 2 to 25 minutes using a mixer;

(2) wet granulating the powder blend by adding a solution of ethanol/water to the powder blend while mixing over a 1 to 30 minute period to form granules;

(3) drying the granules to remove water with heated air in a fluid bed dryer or tray dryer for 10 minutes to 24 hours;

(4) milling the dried granules to a uniform size;

(5) adding and blending a disintegrant with the dried milled particles for 2 to 30 minutes;

(6) adding and blending a lubricant to the mixture containing the disintegrant for 30 seconds to 20 minutes; and (7) compressing the lubricated granules mixture into a desired tablet form.

18. The process of claim 17 wherein the active ingredient is N-[1(R)-[(1,2-dihydro-1-methanesulfonylspiro[3H-indole-3,4'-piperdin]-1'-yl)carbonyl]-2-(phenylmethyloxy)ethyl]-2-amino-2-methyl-propanamide methanesulfonate.

19. The process of claim 18 further comprising coating the tablet by:

(1) dry blending titanium dioxide with hydroxypropyl methylcellulose and hydroxypropyl cellulose to form a dry powdered blend;

(2) adding the dry powdered blend to water to form a slurry;

(3) adding water to the slurry with stirring to form a suspension; and (4) applying the suspension to the tablets.

20. The process of claim 18 wherein the binder/diluent is pregelatinized starch; the first diluent is microcrystalline cellulose; the second diluent is calcium phosphate dibasic; the disintegrant is croscarmellose sodium; and the lubricant is magnesium stearate.

21. The process of claim 14, comprising the steps of:

(1) forming a powder blend of the active ingredient with pregelatinized starch, microcrystalline cellulose, calcium phosphate dibasic, and croscarmellose sodium, in a mixer for about 3 to 25 minutes;

(2) wet granulating the powder blend by adding a solution of 25% ethanol/75% water (w/w) to the powder blend while mixing over a 1 to 30 minute period to form granules;

(3) drying the granules on a tray dryer or a fluid bed dryer for about 1 to 12 hours to remove the ethanol/water;

(4) milling the dried granules to a uniform size using a Quadro Comill or Fitz type mill;

(5) adding and blending croscarmellose sodium with the dried milled particles for about 5 to 30 minutes;

(6) adding and blending magnesium stearate to the mixture containing the croscarmellose sodium with a V blender for about 1 to 5 minutes; and (7) compressing the lubricated granules mixture into a desired tablet form.

22. The process of claim 21 wherein the active ingredient is N-[1(R)-[(1,2-dihydro-1-methanesulfonylspiro[3H-indole-3,4'-piperdin]-1'-yl)carbonyl]-2-(phenylmethyloxy)ethyl]-2-amino-2-methyl-propanamide methanesulfonate.

23. A solid dosage form containing an active ingredient of N-[1(R)-[(1,2-dihydro-1-methanesulfonylspiro[3H-indole-3,4'-piperdin]-1'-yl)carbonyl]-2-(phenylmethyloxy)ethyl]-2-amino-2-methylpropanamide, or a pharmaceutically acceptable salt thereof, wherein the dosage form is prepared by the process of claim 14.

24. An amorphous form of the compound N-[1(R)-[(1,2-dihydro-1-methane-sulfonyl-spiro[3H-indole-3,4'-piperdin]-1'-yl)carbonyl]-2-(phenyl-methyloxy)ethyl]-2-amino-2-methylpropanamide methanesulfonate.

25. The amorphous form of claim 24 characterized by an X-ray diffraction pattern exhibiting an amorphous halo.

26. The amorphous form of claim 24 characterized by showing no biorefringence upon examination under microscopy.

27. An amorphous form of N-[1(R)-[(1,2-dihydro-1-methanesulfonyl-spiro[3H-indole-3,4'-piperdin]-1'-yl)carbonyl]-2-(phenylmethyl-oxy)ethyl]-2-amino-2-methyl-propanamide methanesulfonate which is produced by the process of claim 14.

28. A pharmaceutical composition comprising a pharmaceutically acceptable carrier and an effective amount of the amorphous form of claim 24.

* * * * *